(12) United States Patent
Hausmann et al.

(10) Patent No.: US 8,905,017 B2
(45) Date of Patent: Dec. 9, 2014

(54) RESERVOIR AND ATOMIZER

(75) Inventors: Matthias Hausmann, Rees (DE); Carsten Henning, Recklinghausen (DE); Heinrich Kladders, Muelheim-Ruhr (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 291 days.

(21) Appl. No.: 13/256,728

(22) PCT Filed: Mar. 12, 2010

(86) PCT No.: PCT/EP2010/001573
§ 371 (c)(1),
(2), (4) Date: Dec. 1, 2011

(87) PCT Pub. No.: WO2010/105775
PCT Pub. Date: Sep. 23, 2010

(65) Prior Publication Data
US 2012/0132198 A1 May 31, 2012

(30) Foreign Application Priority Data
Mar. 17, 2009 (EP) .................................... 09003818

(51) Int. Cl.
A61M 11/00 (2006.01)
B05B 9/03 (2006.01)
B65D 41/00 (2006.01)
A61M 11/06 (2006.01)
B05B 11/00 (2006.01)
A61M 15/00 (2006.01)
A61J 1/14 (2006.01)

(52) U.S. Cl.
CPC ......... *B05B 11/0054* (2013.01); *B05B 11/3091* (2013.01); *B05B 11/3015* (2013.01); *B05B 11/0043* (2013.01); *A61M 11/005* (2013.01); *A61M 15/0065* (2013.01); *A61M 11/06* (2013.01); *A61J 2001/1431* (2013.01)
USPC ................. 128/200.14; 128/200.21; 239/302; 220/200; 220/254.1

(58) Field of Classification Search
USPC ............. 128/200.14, 203.12, 203.21, 203.28, 128/200.21; 215/354; 220/200, 253, 254.1, 220/254.7, 258.1–258.5, 833–835, 364; 604/408, 411, 415; 239/302, 309, 328, 239/338
See application file for complete search history.

(56) References Cited

U.S. PATENT DOCUMENTS 4,457,455 A * 7/1984 Meshberg ...................... 222/105
5,857,580 A * 1/1999 Iidaka ............................ 215/256
(Continued)

FOREIGN PATENT DOCUMENTS

CA 2319834 A1 9/1999
CA 2362243 A1 8/2000
(Continued)

OTHER PUBLICATIONS
International Search Report, Form PCT/ISA/210, for corresponding PCT/EP2010/001573; date of mailing: Oct. 6, 2010.

*Primary Examiner* — Valerie L Skorupa
(74) *Attorney, Agent, or Firm* — Michael P. Morris; Mary-Ellen M. Devlin

(57) ABSTRACT

A reservoir and a nebulizer having such a reservoir are proposed. The reservoir comprises a closure for a fluid chamber with a medicament formulation that is formed by two closure members welded together. The closure comprises a particle barrier for preventing the ingress into the fluid chamber of any weld particles that may potentially be formed during the welding of the two closure members. The fluid chamber is preferably broadened in the shape of a beaver tail and is sealed lengthways with an additional strip of material.

16 Claims, 10 Drawing Sheets

(56) References Cited

U.S. PATENT DOCUMENTS

| | | |
|---|---|---|
| 6,685,691 B1 | 2/2004 | Freund et al. |
| 6,988,496 B1 | 1/2006 | Eicher et al. |
| 2002/0007155 A1* | 1/2002 | Freund et al. .................. 604/232 |
| 2005/0284839 A1* | 12/2005 | McKenna et al. ............. 215/354 |
| 2012/0132198 A1 | 5/2012 | Hausmann |

FOREIGN PATENT DOCUMENTS

| | | |
|---|---|---|
| EP | 1223115 A1 | 7/2002 |
| JP | 62253068 A | 11/1987 |
| WO | 9943571 A1 | 9/1999 |
| WO | 0049988 A2 | 8/2000 |
| WO | 2010105775 A2 | 9/2010 |

* cited by examiner

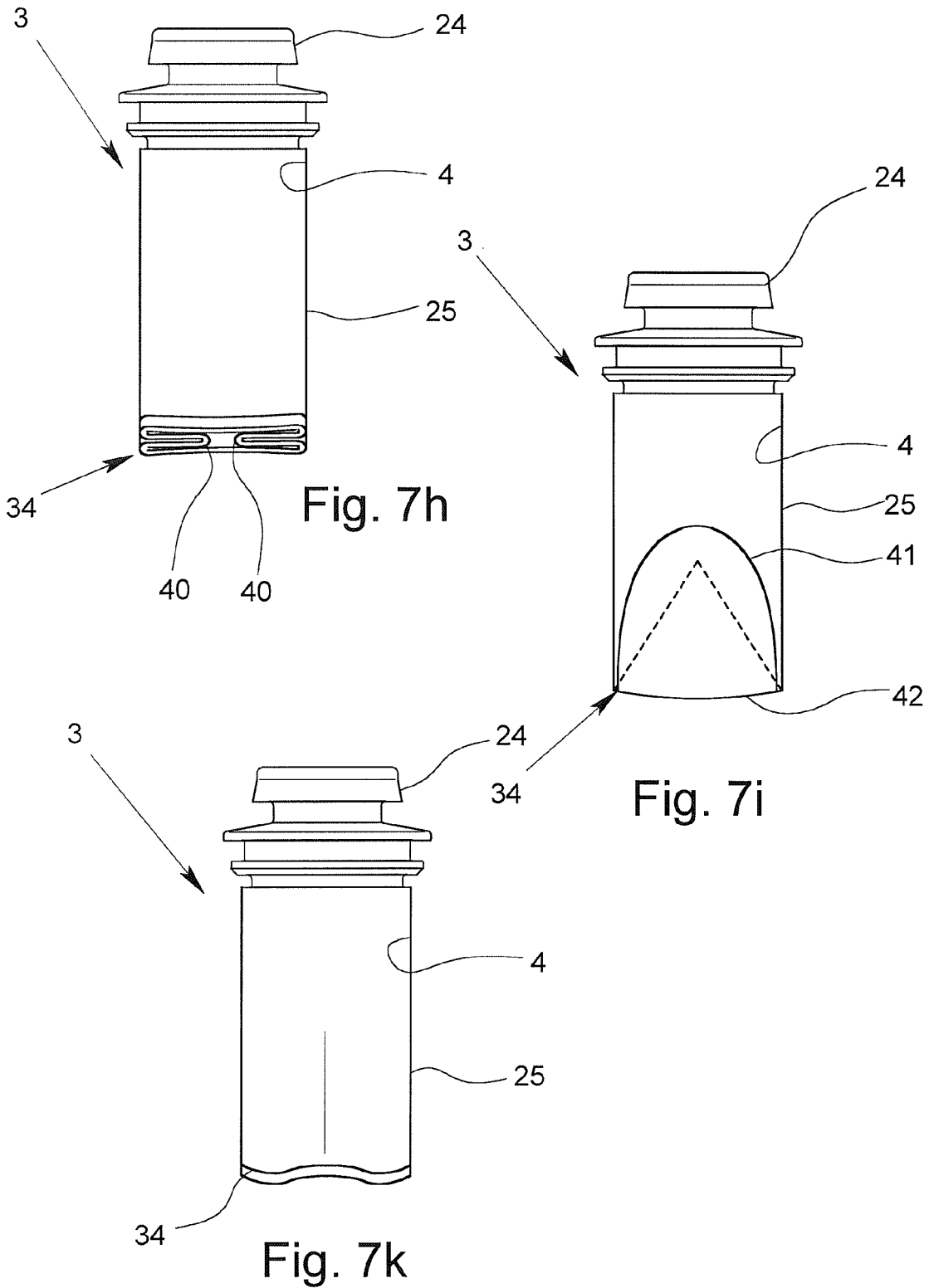

RESERVOIR AND ATOMIZER

The present invention relates to a reservoir according to the preamble of claim 1 or 12 and a nebuliser according to the preamble of claim 15.

A container for a nebuliser or inhaler is known from WO 99/43571 A1. The container has a rigid metallic outer casing and a bag accommodated therein. The bag forms a fluid chamber for a medicament preparation and collapses when the medicament preparation is taken out. The bag is closed off by a preferably two-part seal, particularly in the manner of a flange. A first closure member is fixedly connected to the bag. After the medicament preparation has been introduced through an opening in the first closure member, a second closure member is attached to the first closure member preferably by ultrasonic welding to hermetically seal the medicament preparation or the fluid chamber. In order to remove the medicament preparation, the closure or the second closure member can be pierced by a conveying element which then extends into the fluid chamber.

With the known container there is the potential problem that during the ultrasonic welding of the second closure member to the first closure member, in particular, weld particles (flash) may be formed. These weld particles may penetrate inside the container or the fluid chamber or get into the medicament preparation.

The aim of the invention is to provide a reservoir having a fluid chamber for a fluid, particularly for a medicament preparation, and a nebuliser or inhaler having such a reservoir, while preventing, as simply and efficiently as possible, any particles or other contaminants that may potentially be produced during the sealing of the fluid chamber by the joining of two closure members, particularly by the welding of the closure members, from getting into the fluid or the fluid chamber.

This aim is achieved by means of a reservoir according to claim 1 or a nebuliser provided with this reservoir. Advantageous further features are the subject-matter of the subclaims.

In one aspect of the present invention, the closure of the reservoir or fluid chamber comprises a barrier arranged on the fluid side with respect to an attachment region of the two closure members, to prevent any particles or other contaminants that may potentially be formed during the joining of the closure members from penetrating into the fluid and/or into the fluid chamber. In particular the barrier is formed by a press fit and/or abutment region of the two closure members. This is a very simple and efficient manner of ensuring that any particles or other contaminants that may potentially be formed during the joining of the closure members cannot penetrate into the fluid and/or into the fluid chamber.

A further aim of the present invention is to provide a reservoir having a fluid chamber for a fluid, particularly for a medicament preparation, and a nebuliser or inhaler having such a reservoir, wherein the fluid chamber, while being simple to manufacture and/or having a large volume capacity, is leaktight and/or collapses very easily.

The aim stated above is achieved by a reservoir according to claim 12 or a nebuliser provided with this reservoir.

One aspect of the invention that can also be implemented independently consists in the fact that the fluid chamber broadens out at its free end in particular in the manner of a beaver tail. This contributes to ease of collapse as fluid is taken out, a large volume capacity and/or ease of manufacture.

In another aspect of the present invention that can also be implemented independently the fluid chamber is formed by a wall with a longitudinal seam in which longitudinal edges of a piece of material forming the wall are joined together essentially edge to edge by means of a strip of material—particularly preferably a different and/or additional material. This helps to assist the collapse as fluid is taken out and/or contributes to the ease of manufacture.

The aspects and features of the present invention described above and the aspects and features of the present invention described below may be implemented independently of one another or in any desired combination.

Further advantages, features, properties and aspects of the present invention will become apparent from the claims and the following description of preferred embodiments by means of the drawings, wherein:

Figure 7A:
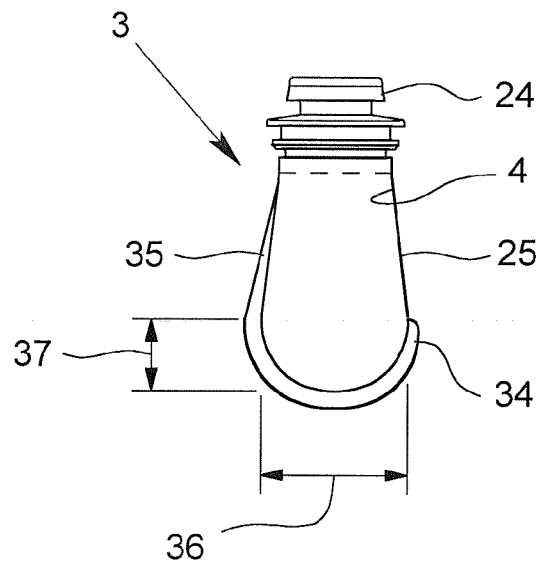
Figure 7B:
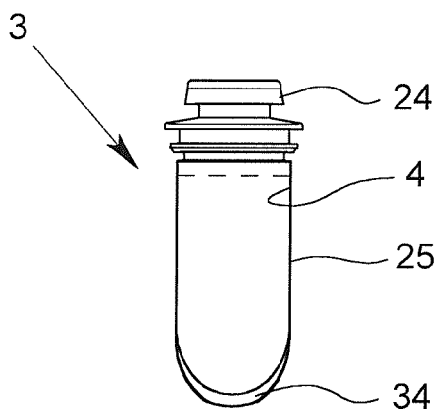
Figure 7C:
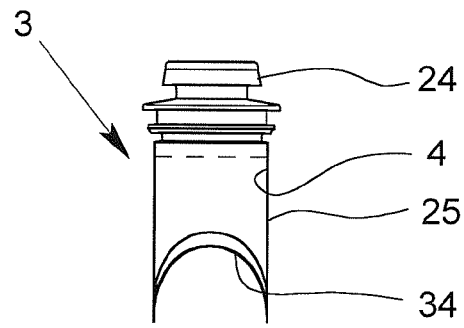
Figure 7D:
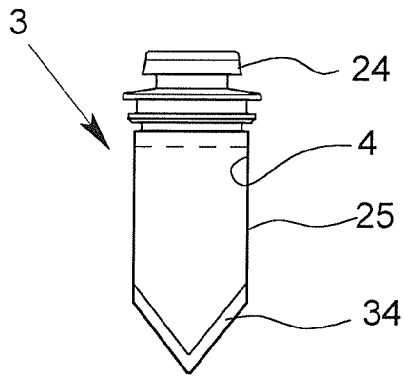
Figure 7E:
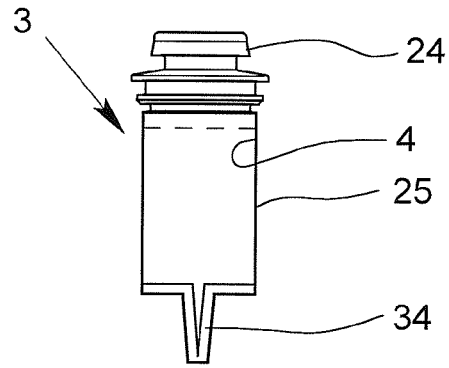
Figure 7F:
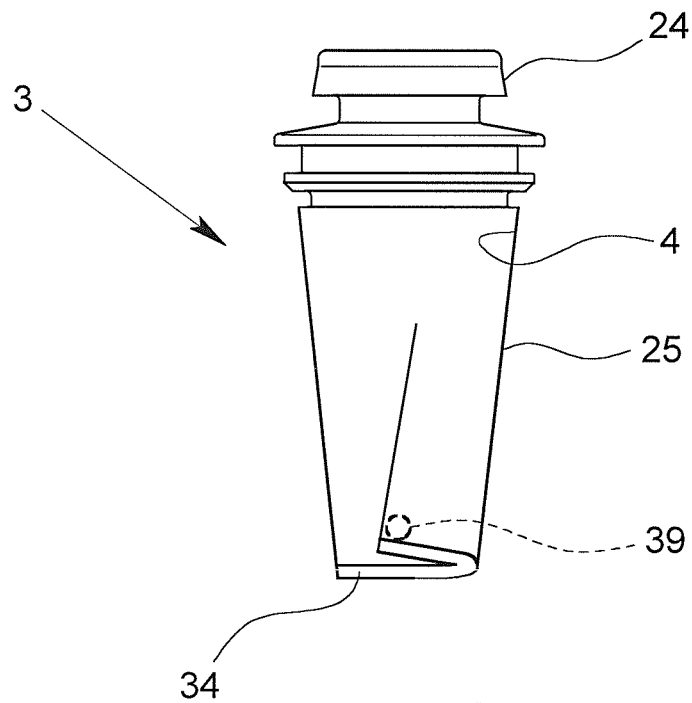
Figure 7G:
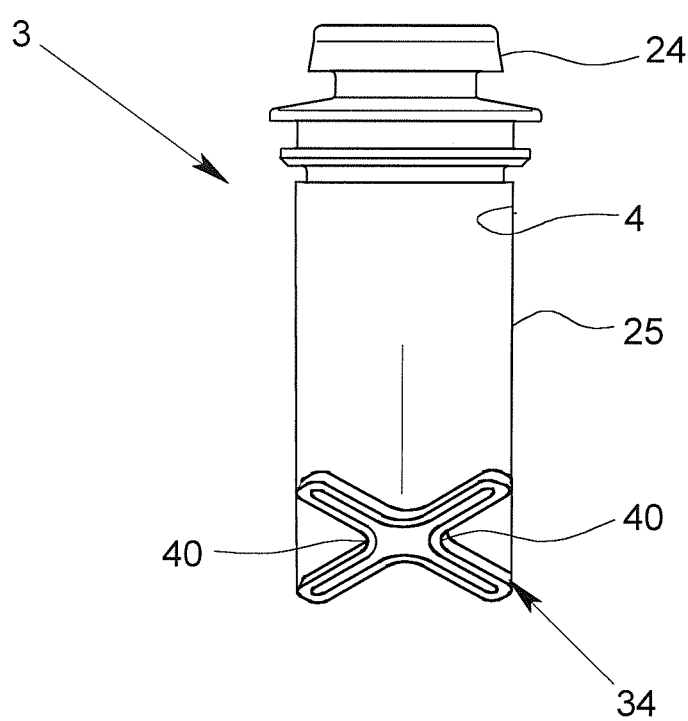
Figure 8A:
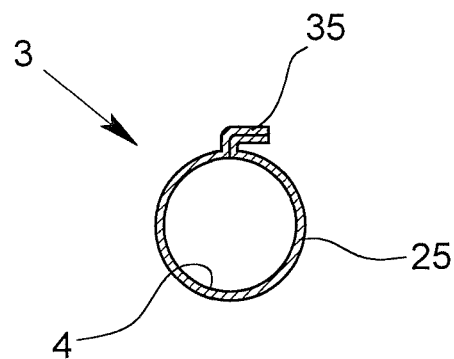
Figure 8B:
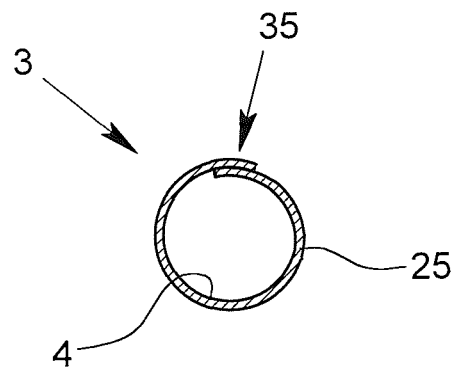
Figure 8C:
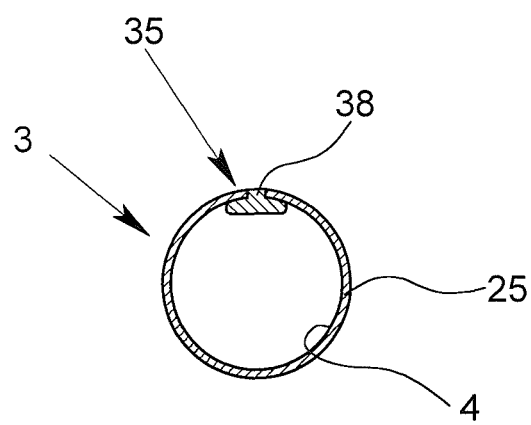

FIGS. 7a-k are schematic representations of different sealing geometries of a fluid chamber of the reservoir; and FIGS. 8a-c are schematic cross-sections through fluid chambers of different constructions.

In the Figures, the same reference numerals have been used for identical or similar components, where, in particular, corresponding or comparable properties and advantages are obtained even though the associated description is not repeated.

Figure 1:
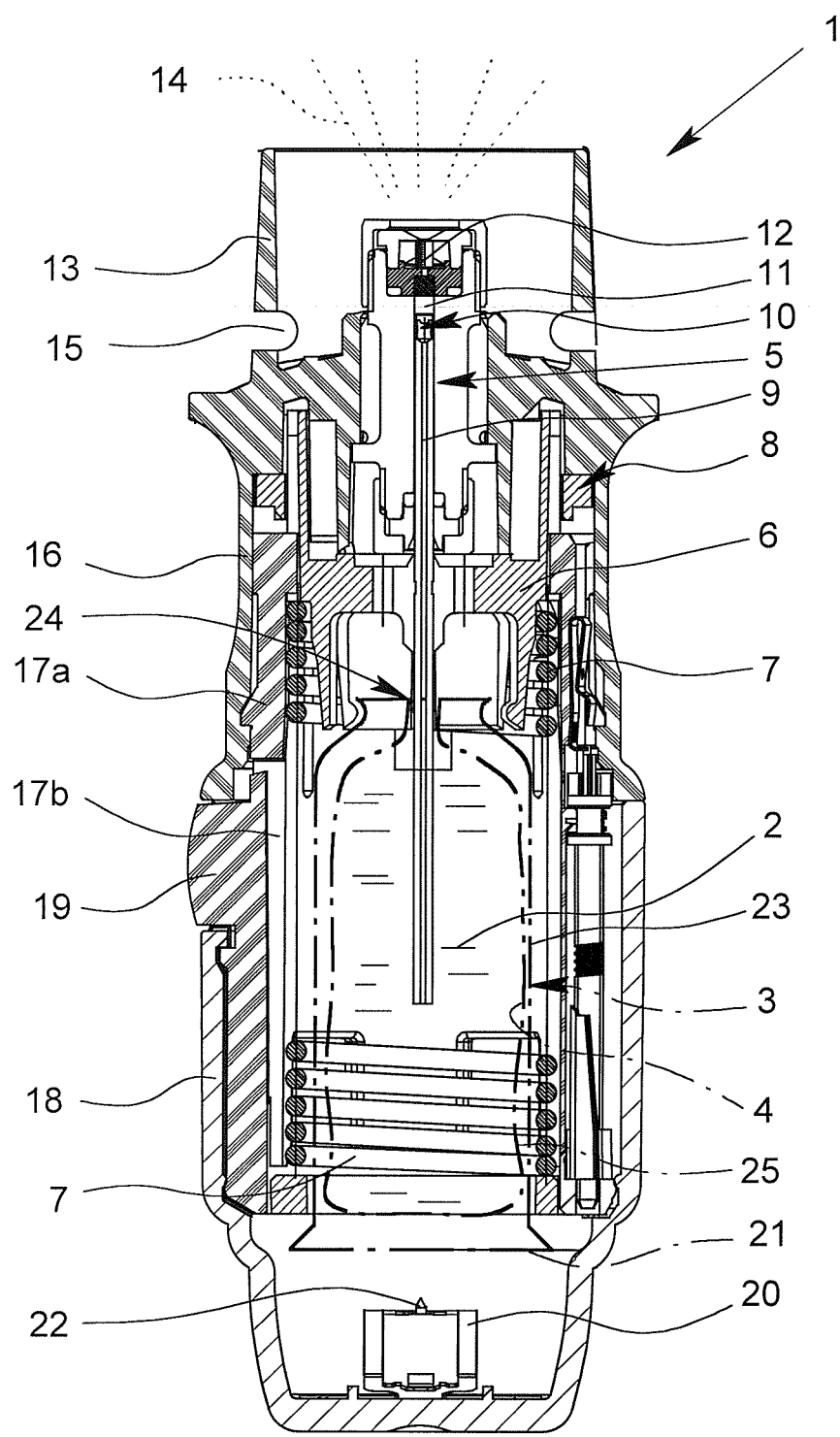
FIG. 1 is a schematic section through a proposed nebuliser in the untensioned state, containing a reservoir of the proposed type.
Figure 2:
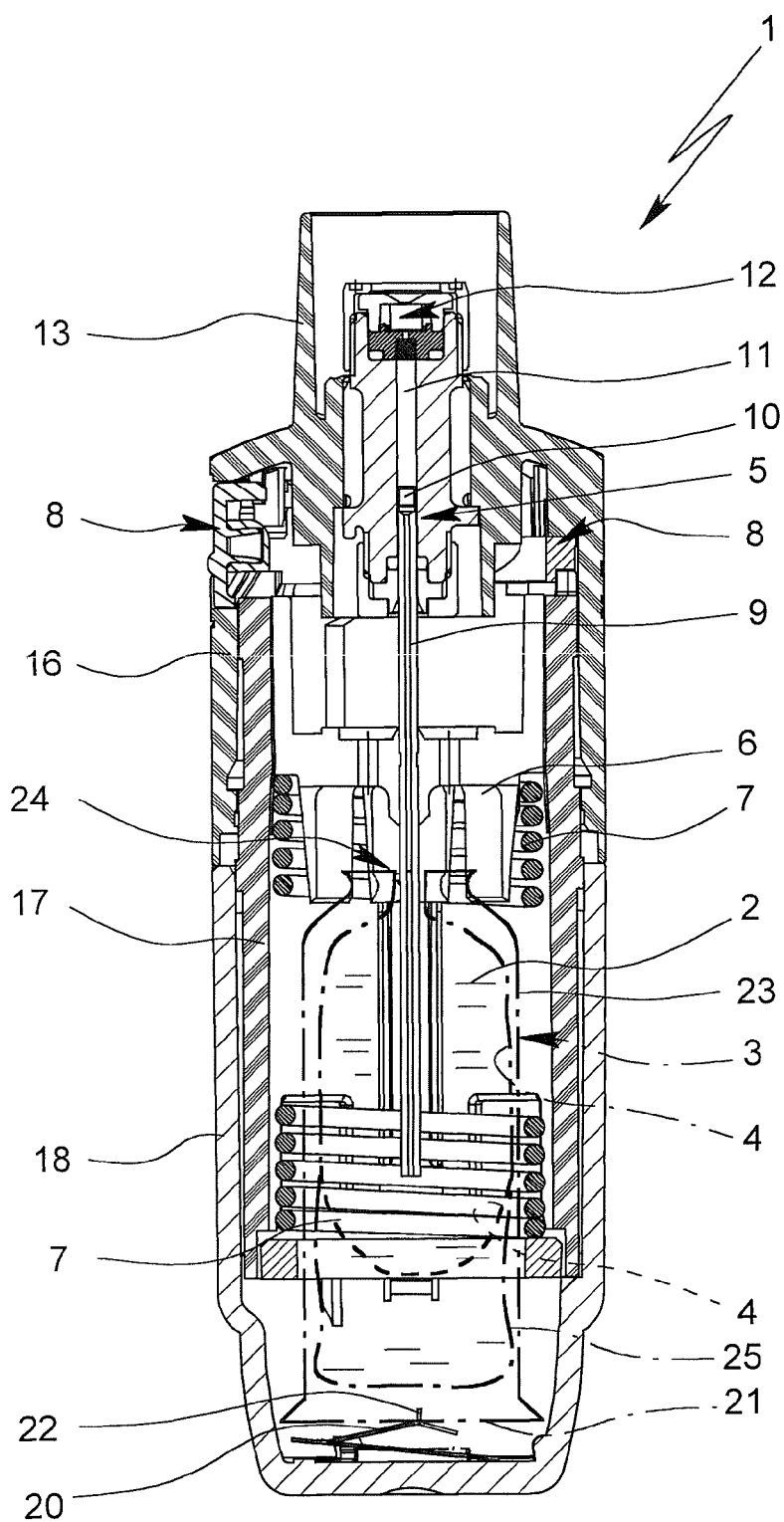
FIG. 2 is a schematic section, rotated through 90° compared with FIG. 1, through the nebuliser in the tensioned state.

FIGS. 1 and 2 show a proposed nebuliser 1 for atomising a fluid 2, particularly a fluid or medicament preparation, in a schematic view in the untensioned state (FIG. 1) and in the tensioned state (FIG. 2). The nebuliser 1 is constructed in particular as a portable inhaler and/or preferably operates without propellant gas.

The atomisation of the fluid 2 or medicament preparation preferably forms an aerosol 14 destined for the lungs (FIG. 1) which can be taken, particularly breathed in or inhaled, by a user or patient (not shown). Usually the preparation is inhaled at least once a day, more particularly several times a day, preferably at set intervals, especially depending on the patient's complaint.

The nebuliser 1 has a preferably insertable and optionally replaceable reservoir 3 containing the fluid 2, as shown in FIGS. 1 and 2. Preferably, the reservoir 3 contains a sufficient quantity (typically 2 to 10 or 2 to 15 ml) of fluid 2 or active substance for a number of doses, i.e. to allow numerous nebulisations or applications.

The reservoir 3 is preferably substantially cylindrical or cartridge-shaped, oblong and/or constructed as an in particular rigid container and/or may be inserted in the nebuliser 1 from below, for example, after the nebuliser has been opened, and may optionally be replaceable.

The reservoir 3 has a fluid chamber 4 containing the fluid 2, which is preferably constructed as a bag or flexible tube. The fluid chamber 4 or a wall 25 bounding the fluid chamber 4 is preferably flexible, deformable and/or collapsible in construction, at least in parts.

The nebuliser 1 preferably has a conveying device, particularly a pressure generator 5, for conveying and/or atomising the fluid 2, particularly in a predetermined, optionally adjustable metering quantity.

The nebuliser 1 or pressure generator 5 comprises in particular a holder 6 for the reservoir 3, an associated drive spring 7, shown only partially, preferably with an associated locking element 8 that is manually operable for unlocking, a conveying element or conveying tube 9 preferably in the form of a capillary, an optional valve, particularly a non-return valve 10, a pressure chamber 11 and/or an expulsion nozzle 12, particularly in the region of a mouthpiece 13 or other end piece.

The reservoir 3 is fixed in the nebuliser 1 by means of the holder 6, particularly by a clamping or latching action, such that the conveying element extends into the fluid chamber 4 and/or is fluidically connected thereto. The holder 6 may be constructed so that the reservoir 3 is replaceable.

When the drive spring 7 is axially tensioned, the holder 6 with the reservoir 3 and the conveying element is moved downwards in the drawings and the fluid 2—more precisely the next dose—is sucked out of the reservoir 3 through the non-return valve 10 into the pressure chamber 11 of the pressure generator 5. The fluid chamber 4 (bag) collapses as a function of the removal of fluid 2, as indicated by way of example and purely schematically by the dashed line in the lower part of the fluid chamber 4 in FIG. 2.

During the subsequent relaxation of the drive spring 7 after actuation of the locking element 8 for atomisation, the fluid 2 in the pressure chamber 11 is put under pressure by the conveying element being moved back upwards, preferably solely by the force of the drive spring 7, with the non-return valve 10 now closed, the conveying element now acting as a pressure ram. This pressure expels the fluid 2 through the expulsion nozzle 12, whereby it is atomised into the aerosol 14 preferably destined for the lungs as shown in FIG. 1.

The user or patient (not shown) can inhale the aerosol 14, while supply air can preferably be taken into the mouthpiece 13 through at least one supply air opening 15.

During the atomisation process or stroke, the reservoir 3 is moved back into its original position by the drive spring 7. The reservoir 3 thus preferably performs a lifting movement during the tensioning process and during the atomisation process.

Instead of the pressure generator 5 and/or drive spring 7 it is also possible to use other means and/or devices.

The nebuliser 1 comprises in particular a first housing part (upper part) 16 and an inner part 17 which is rotatable relative thereto (FIG. 2) having an upper part 17*a* and a lower part 17*b* (FIG. 1), while an in particular manually operable or rotatable second housing part (lower part) 18 is releasably attached to, in particular pushed onto, the inner part 17, preferably by means of a safety lock or holding element 19. In particular, the safety lock or holding element 19 is designed such that there is no possibility of accidentally opening the nebuliser 1 or pulling off the second housing part 18. In particular, in order to release the second housing part 18, the holding element 19 has to be pressed in counter to the force of a spring. For inserting and/or changing the reservoir 3, the second housing part 18 can be detached from the nebuliser 1. The second housing part 18 preferably forms a cap-like lower housing part and/or fits around or over a lower free end portion of the reservoir 3.

The second housing part 18 can be rotated relative to the first housing part 16, carrying the inner part 17 with it. As a result, the drive spring 7 is tensioned in the axial direction by a gear (not shown in detail) acting on the holder 6. As tensioning occurs, the reservoir 3 is moved axially downwards or with its end portion (further) into the second housing part 18 or towards the end face thereof until the reservoir 3 assumes an end position shown in FIG. 2. In this position the drive spring 7 is tensioned.

The nebuliser 1 preferably has means for forcibly venting the reservoir 3, particularly an outer casing 23 of the reservoir 3.

In particular, during tensioning for the first time, the reservoir 3 or the outer casing 23 may be pierced or opened at its base, for example. In the embodiment shown, an axially acting spring 20 arranged in the housing part 18 comes to abut on the reservoir base 21 and uses a piercing element 22 to pierce a bottom seal, particularly a gastight one, for ventilation when it comes to abut for the first time.

The forced ventilation device is thus formed in this case by the piercing element 22 which is held or formed by the spring 20. However, other design solutions are also possible.

It should be noted that during the piercing for venting purposes only the outer casing 23 of the reservoir 3 is opened. The fluid chamber 4 (bag) containing the fluid 2 or the wall 25 remains undamaged.

As the fluid 2 is removed through the conveying element, the flexible or deformable bag or fluid chamber 4 collapses or the wall 25 is deformed. For pressure equalisation, ambient air can flow into the reservoir 3 or outer casing 23 through the venting or piercing opening.

The means for forced venting are provided purely optionally. In particular, the means for forced venting may be omitted altogether, for example if the outer casing 23 of the reservoir 3 is in any case not at least substantially gastight in construction and/or if other venting means are provided, such as a valve or a vent opening that is already open.

In order to use the nebuliser 1, first of all the reservoir 3 must be inserted. This is preferably done by removing or pulling off the second housing part 18. Then the reservoir 3 is inserted or pushed axially into the inner part 17. It is then opened or attached at the head end. This is done by the conveying element, i.e. the conveying tube 9, which pierces a seal of the reservoir 3 preferably provided in particular at the end or head, and/or is subsequently inserted through a closure or connection 24 provided in particular at the head end, preferably with a septum, into the interior of the reservoir 3 or fluid chamber 4. In this way the fluidic connection is formed between the reservoir 3—or more precisely between the fluid chamber 4 in the reservoir 3—via the conveying tube 9, with the pressure generator 5 or with the pressure chamber 11.

Then the second housing part 18 is replaced or pushed back on. The nebuliser 1 can then be tensioned for the first time. Preferably, the reservoir 3 is then pierced, i.e. forcibly vented, at its base by the piercing element 22, as explained previously.

Before being used for the first time, after the reservoir 3 has been inserted or fluidically connected, the nebuliser 1 is preferably tensioned and actuated several times. This so-called priming causes any air present in the conveying element and/or in the pressure generator 5 as far as the expulsion nozzle 12 to be forced out of the fluid 2. The nebuliser 1 is then ready for delivery or inhalation.

FIG. 3 shows in schematic section a particularly preferred construction of the reservoir 3. It should be noted that the diagram is not to scale.

The reservoir 3 or its closure 24 in the embodiment shown preferably has a first closure member 26 and a second closure member 27. The closure 24 preferably consists only of the two closure members 26 and 27 and the optional seal 28. However, other design solutions are also possible.

FIG. 4 shows the reservoir 3 in section at right-angles to FIG. 3 without the optional seal 28.

In the embodiment shown, the outer casing 23 is attached to the first closure member 26, particularly latched thereto. Preferably, the first closure member 26 comprises for this purpose a recess or annular groove 26a into which the outer casing 23 engages with an inner or radial, preferably edge-located projection 23a. However, other design solutions are also possible.

The outer casing 23 is preferably constructed to be at least substantially rigid, oblong and/or cylindrical or hollow-cylindrical, particularly sleeve-shaped.

Figure 3:
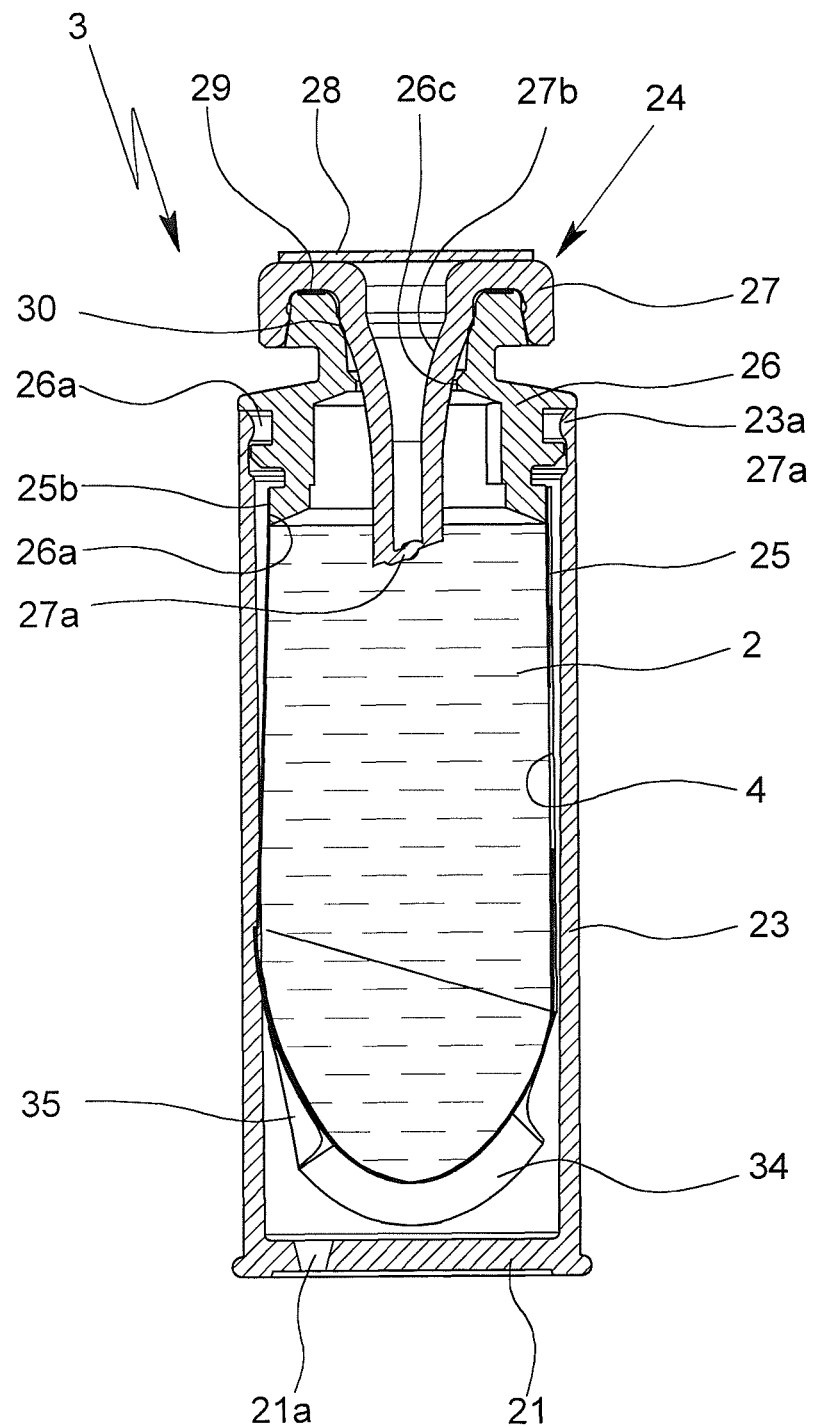
FIG. 3 is a schematic section through the reservoir.

FIG. 3 shows a vent opening 21a in the container base 21 which may optionally be provided. If the vent opening 21a is provided it may be initially closed, for example sealed, to begin with and may be opened by the piercing element 22, for example, when the nebuliser 1 is used for the first time, as described above. However, the vent opening 21a may also be open to begin with. In this case, the opening device or the spring 20 in the lower housing part with the piercing element 22 may be omitted. Instead of the vent opening 21a the outer casing 23 may also be constructed in some other way to be open to the atmosphere or gas-permeable, so as to enable the fluid chamber 4 or the wall 25 to collapse when fluid 2 is taken from the fluid chamber 4.

The fluid chamber 4 or the wall 25 is preferably formed by a tubular or bag-like piece of material. The fluid chamber 4 or the wall 25 may be sealed off at the end opposite the closure 24 before or after the mounting of the closure 24 or the first closure member 26, as desired.

The fluid chamber 4 or its wall 25 is preferably exclusively attached to the first closure member 26 and/or held only at the closure end. For connecting the first closure member 26 to the fluid chamber 4 or wall 25 in a fluidtight and, in particular, gastight manner, the first closure member 26 preferably has an attachment region 26b which is annular or flange-like in construction, in particular, and/or is formed by an outer circumferential surface.

The attachment of the first closure member 26 to the wall 25 or the bag/fluid chamber 4 is preferably carried out before it is filled with fluid 2.

The fluid chamber 4 or the wall 25 is preferably connected to the first closure member 26 or the attachment region 26b thereof in a fluidtight and, in particular, gastight manner in an end or annular region 25a. This attachment is particularly preferably achieved by thermoforming or hot-forming of the first closure member 26 and/or in the manner of a seal, particularly by the effect of heat and pressure, and/or in any other suitable way, for example by adhesive bonding, deformation, compression and/or welding. In the embodiment shown the first closure member 26 is preferably inserted as a preform in an open end or the annular region 25a of the fluid chamber 4, which is in particular still tubular or sleeve-shaped, or the wall 25, and then firmly attached to the wall 25—in this case the inside of the wall 25 in the annular region 25a—by thermoforming or hot-forming.

Preferably, the fluid 2 is introduced into the fluid chamber 4 through a fill opening 26c of the first closure member 26. Then the closure 24 is sealed off by putting on the second closure member 27 and attaching it to the first closure member 26. However, in principle it is also possible to add the fluid 2 from the other end of the fluid chamber 4 only after the closure 24 has been sealed and only then to close off this end of the fluid chamber 4 or wall 25.

The second closure member 27 preferably comprises a septum 27a and/or a fill opening 27b for a conveying element, such as the conveying tube 9, of the nebuliser 1 for taking fluid 2 out of the fluid chamber 4.

In order to close off the closure 24 the second closure member 27 is preferably introduced or inserted into the fill opening 26c of the first closure member 26—particularly with the septum 27a first—and/or placed on the first closure member 26.

The two closure members 26, 27 are then joined together in an attachment region 29 in a fluidtight and in particular gastight manner. In particular, the two closure members 26, 27 are welded in the attachment region 29, particularly preferably by ultrasonic welding. However it is theoretically also possible to join the two closure members 26, 27 together in some other way in the connecting region 29 in order to close off the closure 24 and in particular to seal the fluid chamber 4 hermetically in the attachment region 29.

The attachment region 29 is preferably of circumferential or annular configuration. In particular, the attachment region 29 concentrically surrounds the fill opening 26c and/or insertion opening 27b.

Figure 4:
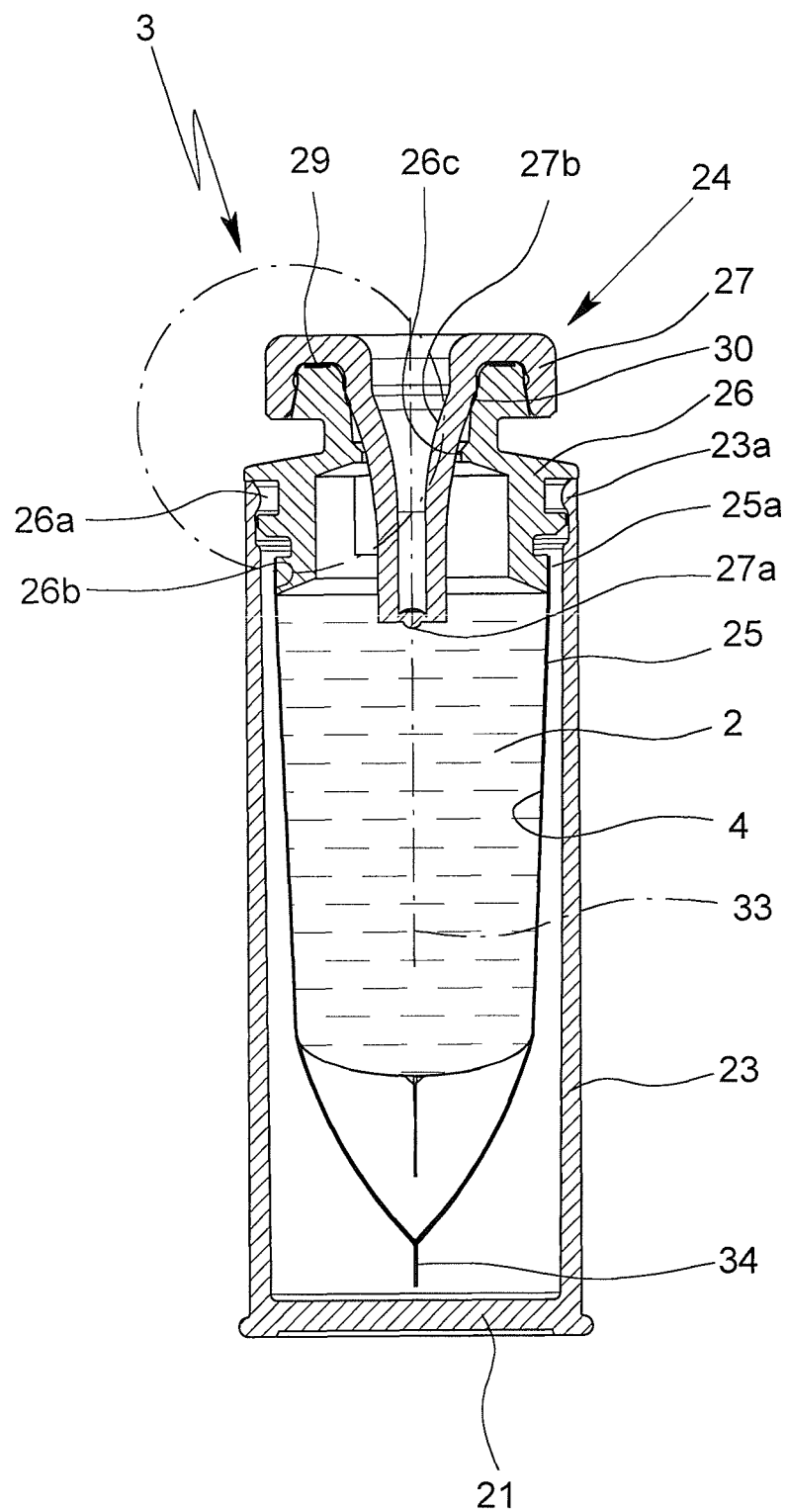
FIG. 4 is another schematic section through the reservoir.
Figure 5:
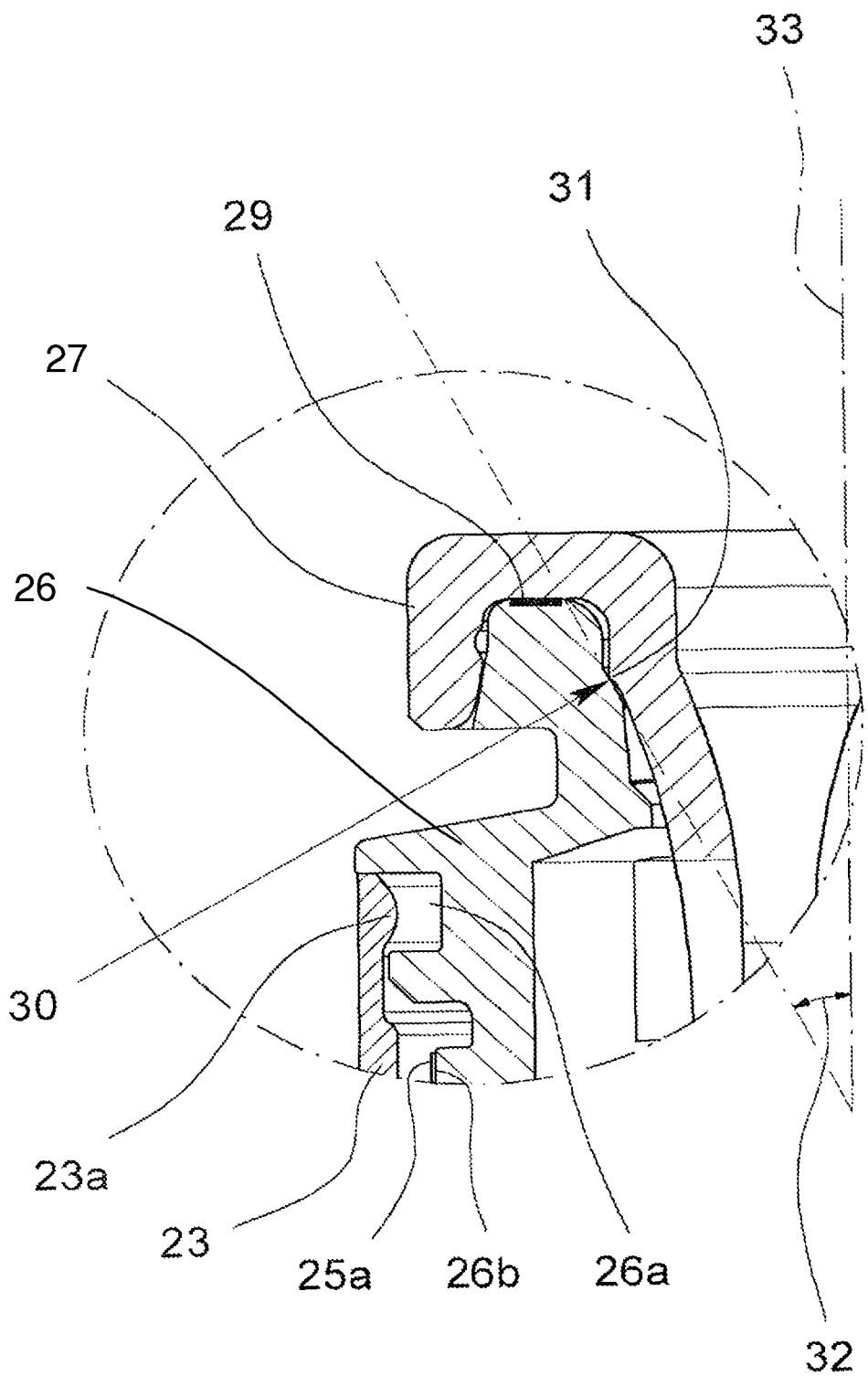
FIG. 5 is a magnified detail from FIG. 4.

Particularly preferably, the attachment region 29 is formed between two substantially radially extending and axially superimposed flange portions of the two closure members 26, 27, as indicated in particular in FIG. 5, which shows a magnified detail from FIG. 4. However, here again, other design solutions or arrangements or configurations of the attachment region 29 are also possible.

Figure 6:
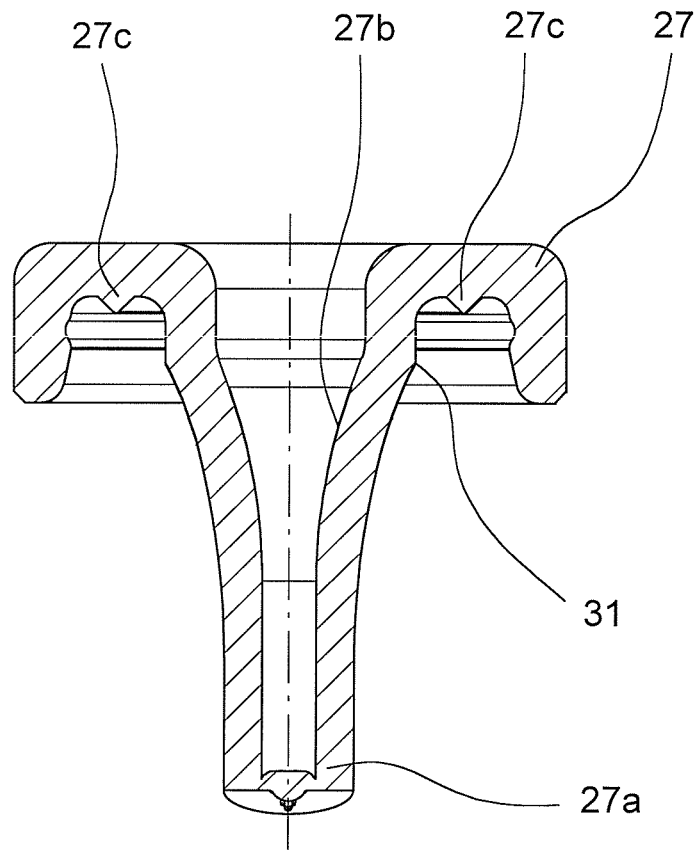
FIG. 6 is a section through a second closure member of a closure of the reservoir.

FIG. 6 shows, in an enlarged section, the second connecting member 27 before installation, i.e. separately. FIG. 6 shows how the second closure member 27 preferably comprises an annular bead 27c or the like—in this case with a tapering and/or, in particular, substantially triangular cross-section—in order to provide the material for welding the two closure members 26, 27 together.

The two closure members 26, 27 are preferably made from a suitable and/or identical plastics material, particularly polyethylene, or some other suitable material. The material that is melted on or fused in order to join the two closure members 26 and 27 together may be provided by the optional annular bead 27c, as already mentioned or in some other way, or may be added during the attachment process. For example, the material may form a ring. The material may be sprinkled or flaked on. The material may correspond to the material of the first and/or second closure member 26, 27 or may contain components thereof. However, the bonding material may also be a different material or a material with a different composition. Depending on the process, the material may also have a different melting temperature from the material of the first and/or second closure member 26, 27.

As already mentioned, the two closure members 26, 27 are preferably attached by welding, particularly ultrasonic or laser welding. The material that is preferably provided by the optional annular bead 27c and/or other material is then melted or fused and bonds the two closure members 26, 27 in the attachment region 29, as schematically shown in FIGS. 3 to 5.

The reservoir 3 or the closure 24 comprises a barrier 30 for preventing the penetration of particles that may be formed during the sealing of the closure 24 or the attachment of the closure members 26, 27, such as weld particles or flash, or other contaminants, into the inside of the reservoir 3 or the fluid 2 and/or into the fluid chamber 4. Primarily, the barrier 30 serves to prevent the penetration of particles, and therefore will also be referred to hereinafter as the particle barrier, even if it is additionally or alternatively capable of preventing or at least minimising the penetration of other contaminants.

The barrier 30 is particularly preferably formed by a snug fit, force fit or press fit and/or abutment region 31 of the two closure members 26, 27, as indicated in the magnified view shown in FIG. 5.

Preferably, between the two closure members 26, 27 is formed a preferably at least substantially radial snug fit, force fit or press fit which forms the barrier 30.

The barrier 30 is preferably of annular construction. The barrier 30 is preferably formed by parts with blunt geometries that abut on one another; in the embodiment shown only obtuse angles or smooth or rounded surfaces are provided which come to rest or abut on one another to form the barrier 30, particularly in order to prevent unwanted welding in the region of the barrier 30. Particularly preferably, the closure members 26, 27 are not firmly attached or welded in the region of the barrier 30.

In the embodiment shown the attachment of the two closure members 26, 27 in the attachment region 29 is carried out substantially axially, i.e. at right angles and in particular at least substantially perpendicular to the fit or clamping of the barrier 30. This makes it possible for the barrier 30 to be in operation already during the attachment, particularly welding, of the two closure members 26, 27 and the associated movement in the direction of attachment (in the embodiment shown at least substantially perpendicular to the surface extent of the attachment region 29 or at least substantially in the direction of the axis 33 of the container 3 or closure 24 or the direction of insertion of the conveying element as indicated in FIGS. 4 and 5), in other words for the two closure members 26, 27 to form the barrier 30 at least substantially along the entire weld line.

In the embodiment shown, the ultrasonic oscillations for the welding preferably act at least substantially axially or in the longitudinal direction of the reservoir 3. The friction downwards or in the axial direction or in the attachment region 29 then brings about the welding. If the two closure members 26 and 27 are not welded ultrasonically but attached in some other way, for example by laser welding, the barrier 30 or the region that forms the barrier 30, particularly of the first and/or second closure member 26, 27, may also have a different geometry and may for example be formed by a funnel-shaped or lip-like geometry and/or radial sealing geometry, particularly preferably in the manner of a shaft seal.

Generally, the direction of connection of the two closure members 26, 27 thus extends at right-angles or perpendicularly to the clamping or clamping force or fit that produces the barrier 30, preferably between the two closure members 26, 27.

In the embodiment shown the closure members 26, 27 for forming the barrier 30 or in the abutment region have preferably been pushed conically into one another. Particularly preferably, the abutment region 31 or at least one abutment portion formed by the first or second closure member 26 or 27 extends slightly conically, particularly inclined at an angle 32 to an axis 33, as schematically shown in FIG. 5.

The axis 33 runs at least substantially in the direction of the longitudinal axis of the reservoir 3, in a direction of assembly of the two closure members 26, 27, perpendicularly to the flat extent of the attachment region 29, axially with respect to the closure 24 and/or in the preferred direction of introduction of the conveying element into the reservoir 3.

The angle 32 preferably substantially corresponds to the ratio of the weld line to the dimensions of the gap required between the second closure member 27 and the first closure member 26 in the region of the barrier 30 when the second closure member 27 is fitted on before the welding.

The angle 32 is preferably less than 30°, more particularly less than 20°, particularly preferably about 15° or less.

The terms "radial" and "axial" in the present invention preferably refer generally to the direction or axis 33 already mentioned.

As has already been mentioned, the barrier 30 is arranged on the fluid side and is separate from the attachment region 29 such that the barrier 30 (adequately) seals off the fluid chamber 4 against the ingress of particles such as weld particles (not shown) or other contaminants such as may occur when the two closure members 26, 27 are joined together, particularly by welding.

The barrier 30 is preferably sufficiently spaced apart from the attachment region 29 to prevent the two closure members 26, 27 from also being welded in the region of the barrier 30 when the two closure members 26, 27 are welded in the attachment region 29 (particularly by ultrasonic welding).

Preferably, the barrier 30 is at an axial and/or radial spacing from the attachment region 29.

The barrier 30 is preferably arranged within the attachment region 29 and/or closer to the fluid chamber 4 than the attachment region 29.

The barrier 30 is preferably of circumferential or annular configuration and is arranged in particular concentrically with respect to the attachment region 29.

The barrier 30 is preferably embodied such that the abutment region 31 tapers from the free end of the closure 24 to the inside of the fluid chamber 4. However, other design solutions are also possible.

The wall 25 is at least substantially or partially deformable or flexible, to allow the fluid chamber 4 to collapse as easily as possible when fluid 2 is taken out. In fact, the fluid chamber 4 is sealed off in at least substantially gastight manner. The wall 25 is accordingly formed to be substantially gastight.

The wall 25 is preferably of multi-layered construction, and in particular the wall 25 comprises a preferably metallic barrier layer (particularly a metal film) and an inner layer and optionally further layers. The individual layers may be formed for example by coating, lamination or other suitable means. The barrier layer is embodied in particular as an aluminium layer or film.

Particularly preferably, the wall 25 or the film material used has an outer protective layer, preferably of PET, a preferably metallic intermediate or barrier layer, particularly of aluminium, and an inner layer, particularly of PE.

The wall 25 or its layered structure is preferably embodied as a film or made from film material.

During manufacture, first a sleeve or hollow cylindrical shape or a tube is formed from the wall 25 or from the film material that forms the wall 25, particularly by longitudinal welding of a corresponding strip of material.

After any required cutting to length, in the case of a continuous manufacturing process, the sleeve-like pieces are each sealed in order to form the respective fluid chamber 4.

The closure 24 seals the reservoir 3 or the fluid chamber 4 at a first end, particularly in a head region or at the end face.

Preferably, first of all the closure 24 or the closure member 26 is provided, particularly preferably attached by injection moulding or shaping. To do this, a suitable material is preferably chosen for the closure member 26, such as a PE (polyethylene) or a PET (polyethylene terephthalate) which attaches itself to the wall 25. For example, the closure member 26 may attach itself directly to the inside of the wall 25.

Preferably, the wall 25 is only firmly or non-releasably attached to the closure member 26.

The fluid chamber 4 or the wall 25 is sealed, in particular, in an end region opposite the closure 24, particularly by welding, sealing or the like of the wall 25, thus forming a transverse seam 34, as indicated in FIGS. 3 and 4. This closing off of the fluid chamber 4 at the end may be carried out either before or after the fitting of the closure 24 or closure member 26, as selected.

The closing of the fluid chamber 4 at the free end is preferably carried out after the fitting of the closure member 26 or after the fitting of the closure 24. However, the closing of the reservoir 3 or fluid chamber 4 at the opposite end to the closure 24 may also be done first, i.e. before the fitting of the closure member 26.

The filling of the reservoir 3 or the fluid chamber 4 with the fluid 2 may be carried out as desired either through the closure 24—i.e. the actual removal end—or through the other end, in this case, the bottom end or free end. In the former case the fluid 2 is filled with the fluid 2 before the closure 4 is sealed, particularly before the insertion of the second closure member 27 (the closure member 27 is preferably welded in gastight manner to the closure member 26 to seal the closure 24).

Various preferred embodiments of the fluid chamber 4 or wall 25 will now be described by reference to the purely schematic representations in FIG. 7. These representations all show the reservoir 3 without the outer casing 23.

FIG. 7a shows a particularly preferred form of the fluid chamber 4 or wall 25. In addition to the transverse seam 34 an optional longitudinal seam 35 of the fluid chamber 4 or wall 25 is shown here. In this bag-shaped embodiment, the maximum width 36 in the region of the end of the fluid chamber 4 remote from the closure 24 or in the region of the transverse seam 34 is preferably greater than the diameter of the closure 24 or the wall 25 towards the closure 24. The alternative embodiment in FIG. 7a allows an optimum or very high fill volume to be achieved, in particular.

The fluid chamber 4 preferably comprises a rounded and/or flat end in the region of the transverse seam 34. However, the transverse seam 34 may also, for example, run crosswise or straight and optionally also diagonally.

Preferably, the transverse seam 34 merges into the longitudinal seam 35.

In the present embodiment, the spacing 37 of the region of maximum diameter 36 or maximum width 36 towards the free end of the fluid chamber 4 is preferably less than the diameter of the closure 24 or the fluid chamber 4 in the region of the closure 24.

When the reservoir 3 is assembled or the bag or fluid chamber 4 is installed in the outer casing 23, the wall 25 is radially compressed or folded such that the width 36 is reduced sufficiently for the wall 25 to fit into the outer casing 23, as schematically shown in the section according to FIG. 3. The optional longitudinal seam 35 is preferably folded or wrapped round.

The other longitudinal section according to FIG. 4 shows that the fluid chamber 4 or the wall 25 preferably decreases or becomes flatter, respectively, in width or thickness, going from the closure 24 to the other end, particularly preferably forms a comparatively flat free end. When fluid 2 is taken out of the fluid chamber 4, the fluid chamber 4 collapses further in this transverse direction, in particular. However other types of deformation are also possible.

In the alternative embodiment according to FIG. 7b the fluid chamber 4 or the wall 25 has an at least substantially constant diameter over its entire axial extent.

In the alternative embodiment according to FIG. 7b the transverse seam 34 is preferably more rounded or has a smaller radius of curvature than is the case with the embodiment according to FIG. 7a. This may contribute to an easier collapse and/or assist with the collapse.

In the alternative embodiment according to FIG. 7c the fluid chamber 4 or the wall 25 has a preferably convex transverse seam 34. This may reduce tensions in the region of the transverse seam 34, in particular.

In the alternative embodiment according to FIG. 7d the fluid chamber 4 or the wall 25 has a transverse seam 34 which preferably extends at least substantially in a V-shape and/or diagonally. As already mentioned, the transverse seam 34 may also extend substantially only straight (either substantially perpendicular or diagonally or at an angle to the longitudinal axis 33 of the reservoir 3 or direction of insertion, which is not shown here).

In the alternative embodiment according to FIG. 7e the transverse seam 34 is at least substantially T-shaped. This simplifies the configuration of sealing cheeks (not shown) to form the transverse seam 34 and/or the manufacturing process.

In the alternative embodiment according to FIG. 7f the fluid chamber 4 or the wall 25 is folded after sealing, in this case particularly preferably folded longitudinally, at least in the region of the free end or the transverse seam 34. Particularly preferably, the folding is carried out such that the fluid chamber 4 has an outer contour that tapers and/or at least does not substantially increase towards the free end, so as to assist or allow the positioning of the outer casing 32.

In the alternative embodiment shown, the fluid chamber 4 or the wall 25 comprises a transverse seam 34 which extends at least substantially straight and/or at right-angles to the longitudinal extent. However, other configurations or shapes of transverse seams are also possible here.

For holding or securing the bag or fluid chamber 4 in the folded state at least temporarily for assembly or for the positioning of the outer casing 23, in the embodiment shown a securing or connecting means is preferably provided which in this case is produced particularly preferably by partial adhesive bonding on the outside, as schematically indicated by the preferably dot-type adhesive region 39 in FIG. 7f. A hot-melt adhesive is used in particular for the gluing. However, it is also possible to use a strip or other outer fixing means, for example a ring that is pushed on, or another insertion aid, to bring the bag or fluid chamber 4 at least temporarily into a desired shape for installation in the outer casing 23 or to hold it therein or at least limit its external expansion. However, an insertion or assembly aid of this kind may also be obtained additionally or alternatively by means of a separate tool (not shown), for example an insertion funnel, which ensures a corresponding shaping and/or guidance of the bag or fluid chamber 4, for example, when the bag or fluid chamber 4 is introduced into the outer casing 32.

A particular advantage of the alternative embodiment according to FIG. 7f is that it is possible to achieve a high dimensional stability of the fluid chamber 4 or wall 25 for insertion into the outer casing 23.

In the alternative embodiment according to FIG. 7g the transverse seam 34 preferably extends three-dimensionally. In particular, during manufacture, three-dimensional shaping takes place as a result of the lie of the transverse seam 34 or the parts of the wall 25 that are joined together by the transverse seam 34.

In the alternative embodiment according to FIG. 7g a transverse seam 34 is formed which is preferably at least substantially X-shaped in front elevation.

A particular advantage is that it is possible to achieve a high dimensional stability of the fluid chamber 4 or the wall 25 for insertion into the outer casing 23.

In the alternative embodiment according to FIG. 7h the fluid chamber 4 or the wall 25 is folded in longitudinally at least in the region towards the free end or towards the transverse seam 34, particularly on opposite sides, as shown diagrammatically by the bends or indentations or inward folds 40. This is particularly preferably achieved by corresponding shaping of the transverse seam 34 or three-dimensional transverse seam 34 or welding or sealing of the ends of the piece of material/film that is in the fluid chamber 4 or forms the wall 25. In this way it is possible to obtain a relatively high dimensional stability of the fluid chamber 4 or wall 25 for insertion into the outer casing 23.

In the alternative embodiments described hereinbefore the welding or sealing or other closing of the bag or fluid chamber 4 may particularly preferably be carried out in one plane. Other three-dimensional shapes of transverse seams are described hereinafter in which the welding, sealing or other method of attachment is carried out not in one plane but in a three-dimensional spatial form. It is particularly advantageous to be able to achieve a very high dimensional stability of the fluid chamber 4 or the wall 25, particularly towards the free end or in the region of the transverse seam 34, and/or if the diameter of the fluid chamber 4 or the wall 25 can be specified or influenced in highly defined manner towards the free end or in the region of the transverse seam 34, in particular if it does not change or, if necessary, decreases towards the free end. Moreover, the shape of the free end can be optimised in particular with respect to ease of insertion in the outer casing 23, for example by means of a tapering shape.

In the alternative embodiment according to FIG. 7i one side of the wall 25 or the piece of material is pressed in at the free end until it abuts on the other side. The upper edges of the two sides do not come to rest one on top of the other, but rather the edge of the side that is pressed in is set back inwardly to some extent on the side that is not pressed in. The transverse seam 34 thus formed is shown purely schematically. It is made up, for example, of a substantially parabolic part 41 and a substantially arcuate part 42.

However, other three-dimensional configurations are also possible. For example, the pressing in of one side towards the other sides at the end of the fluid chamber 4 or the wall 25 may be carried out so as to achieve not a round shape but an at least substantially angular, particularly preferably V-shaped or triangular shape or outer contour, as indicated by dashed lines in FIG. 7i. Particularly preferably, the bag or fluid chamber 4 or the transverse seam 34 is then substantially V-shaped in front elevation, the enclosed angle then being particularly preferably less than 75°, so that the bag or fluid chamber 4 also fits directly into the outer casing 23.

FIG. 7k shows another alternative embodiment with a corrugated end to the bag or fluid chamber or with a three-dimensionally corrugated transverse seam 34. Here, too, the shaping of the transverse seam 34 can ensure that the bag or fluid chamber 4 fits directly into the outer casing 23.

Generally it should be noted that the fluid chamber 4 or the wall 25 has an at east substantially oblong shape, preferably tapering towards the free end, and/or cylindrical shape, thus facilitating assembly, particularly the putting on of the outer casing 23 or insertion into the outer casing 23. However, other design solutions are also possible.

It should also be generally remarked that a defined folding of the bag or fluid chamber 4 and/or the three-dimensionally defined transverse seam 34 can prevent undesirable or undefined kinking of the bag or fluid chamber during the filling. This is particularly important when filling is carried out at least substantially without pressure and/or if a defined expansion is to be ensured before filling, for example by inflation.

As already mentioned, the bag or fluid chamber 4 may also be generally folded after the transverse seam 34 has been produced. This may be carried out as desired either before or after filling with fluid 2 and/or expansion by inflation. Thus, in particular, it can be ensured that the bag or fluid chamber 4 assumes a shape that allows, or at least facilitates, insertion into the outer casing 23.

Alternatively or additionally, an insertion tool (not shown) such as an insertion funnel or the like may be used to allow or facilitate the assembly, particularly the placing of the outer casing 23 over the bag or fluid chamber 4.

Alternatively or additionally, the outer casing 23 may if necessary also be temporarily deformed, for example flattened to some extent at its receiving end, in order to be able to receive the bag or fluid chamber 4 better or more easily. This would, in particular, assist with or permit the insertion of the bag or fluid chamber 4 that is in the shape of a beaver tail or broadened out towards the free end (as in FIG. 7a, for example).

As already mentioned, the fluid chamber 4 or the wall 25 is preferably made from an oblong strip of material which is sealed along its longitudinal sides, particularly welded longitudinally, to form the preferably bag-shaped or tubular or sleeve-like fluid chamber 4. FIG. 8 shows representations of two possible alternative embodiments of the longitudinal welding. The fluid chamber 4 or wall 25 is shown in each case in a purely schematic cross-section, not to scale, without the outer casing 23 and without the transverse seam 34.

In the embodiment according to FIG. 8a, the piece of material that forms the wall 25 is joined along its longitudinal sides by the radially protruding longitudinal seam 35. The longitudinal seam 35 is preferably wrapped round or folded round, as indicated purely diagrammatically in FIG. 8a. The joining of the edges of the piece of material in the region of the longitudinal seam 35 is preferably carried out by welding, particularly by ultrasonic welding, and/or by any other suitable method, for example by heat-sealing, gluing or the like.

According to the embodiment in FIG. 8b, it is also possible to join longitudinal edges of the piece of material that forms the wall 25 by overlapping to form a longitudinal seam 35. In this case, part of the outside is thus joined to the inside of the overlapping region of the piece of material in the region of the overlap.

In the alternative embodiment according to FIG. 8c, the longitudinal edges of the piece of material that forms the wall 25 are joined together substantially edge to edge, to form a longitudinal seam 35, preferably by means of an additional lengthwise strip or strip of material 38, i.e. preferably by seamless longitudinal welding using additional material (this may be for example the same material as an inner covering of the wall 25 or some other material attached thereto).

The fluid chamber 4 or the wall 25 may alternatively also be produced or formed, without a joint along the longitudinal sides, from a corresponding endless tubular material or the like, preferably from a tubular blow-moulded or extruded material.

It should be noted that the reservoir 3 or the preferably bag-like fluid chamber 4 may basically or preferably also be embodied as described in WO 99/43571 A1, which is hereby incorporated by reference as a supplementary disclosure.

In particular, the proposed reservoir 3 and the present invention in general may also be used in the nebulisers or inhalers that are described in the following specifications or are based on the principles therein: EP 1 236 517, EP 1 561 484, EP 1 562 094, EP 1 604 701, JP 2004-0283245, JP 2004-249208, JP 2004-283244, JP 2005-058421, US 2002/0153006, US 2003/0100964, US 2003/0127538, US 2004/0163646, US 2005/0034723, US 2005/0133029, US 2005/0172957, US 2005/0224076, US 2005/0268911, U.S. Pat.

No. 5,915,378, WO 03/041774, WO 2004/022128, WO 2004/039442 and WO 2004/078244.

Preferably the fluid 2 is a liquid, as already mentioned, particularly an aqueous or ethanolic medicament formulation. However, it may also be a different medicament formulation, a suspension or the like, or particles or powders.

Some preferred ingredients, compounds and/or formulations of the preferably medical fluid 2 are listed below. As already mentioned, they may be aqueous or non-aqueous solutions, mixtures, ethanol-containing or solvent-free formulations or the like. The fluid 2 particularly preferably contains:

The compounds listed below may be used in the device according to the invention on their own or in combination. In the compounds mentioned below, W is a pharmacologically active substance and is selected (for example) from among the betamimetics, anticholinergics, corticosteroids, PDE4-inhibitors, LTD4-antagonists, EGFR-inhibitors, dopamine agonists, H1-antihistamines, PAF-antagonists and PI3-kinase inhibitors. Moreover, double or triple combinations of W may be combined and used in the device according to the invention. Combinations of W might be, for example:

W denotes a betamimetic, combined with an anticholinergic, corticosteroid, PDE4-inhibitor, EGFR-inhibitor or LTD4-antagonist, W denotes a corticosteroid, combined with a PDE4-inhibitor, EGFR-inhibitor or LTD4-antagonist W denotes a PDE4-inhibitor, combined with an EGFR-inhibitor or LTD4-antagonist W denotes an EGFR-inhibitor, combined with an LTD4-antagonist.

The compounds used as betamimetics are preferably compounds selected from among albuterol, arformoterol, bambuterol, bitolterol, broxaterol, carbuterol, clenbuterol, fenoterol, formoterol, hexoprenaline, ibuterol, isoetharine, isoprenaline, levosalbutamol, mabuterol, meluadrine, metaproterenol, orciprenaline, pirbuterol, procaterol, reproterol, rimiterol, ritodrine, salmefamol, salmeterol, soterenol, sulphonterol, terbutaline, tiaramide, tolubuterol, zinterol, CHF-1035, HOKU-81, KUL-1248 and 3-(4-{6-[2-hydroxy-2-(4-hydroxy-3-hydroxymethyl-phenyl)-ethylamino]-hexyloxy}-butyl)-benzyl-sulphonamide 5-[2-(5,6-diethyl-indan-2-ylamino)-1-hydroxy-ethyl]-8-hydroxy-1H-quinolin-2-one 4-hydroxy-7-[2-{[2-{[3-(2-phenylethoxy)propyl]sulphonyl}ethyl]-amino}ethyl]-2(3H)-benzothiazolone 1-(2-fluoro-4-hydroxyphenyl)-2-[4-(1-benzimidazolyl)-2-methyl-2-butylamino]ethanol 1-[3-(4-methoxybenzyl-amino)-4-hydroxyphenyl]-2-[4-(1-benzimidazolyl)-2-methyl-2-butylamino]ethanol 1-[2H-5-hydroxy-3-oxo-4H-1,4-benzoxazin-8-yl]-2-[3-(4-N,N-dimethylaminophenyl)-2-methyl-2-propylamino]ethanol 1-[2H-5-hydroxy-3-oxo-4H-1,4-benzoxazin-8-yl]-2-[3-(4-methoxyphenyl)-2-methyl-2-propylamino]ethanol 1-[2H-5-hydroxy-3-oxo-4H-1,4-benzoxazin-8-yl]-2-[3-(4-n-butyloxyphenyl)-2-methyl-2-propylamino]ethanol 1-[2H-5-hydroxy-3-oxo-4H-1,4-benzoxazin-8-yl]-2-{4-[3-(4-methoxyphenyl)-1,2,4-triazol-3-yl]-2-methyl-2-butylamino}ethanol 5-hydroxy-8-(1-hydroxy-2-isopropylaminobutyl)-2H-1,4-benzoxazin-3-(4H)-one 1-(4-amino-3-chloro-5-trifluoromethylphenyl)-2-tert.-butylamino)ethanol 6-hydroxy-8-{1-hydroxy-2-[2-(4-methoxy-phenyl)-1,1-dimethyl-ethylamino]-ethyl}-4H-benzo[1,4]oxazin-3-one 6-hydroxy-8-{1-hydroxy-2-[2-(ethyl 4-phenoxy-acetate)-1,1-dimethyl-ethylamino]-ethyl}-4H-benzo[1,4]oxazin-3-one 6-hydroxy-8-{1-hydroxy-2-[2-(4-phenoxy-acetic acid)-1,1-dimethyl-ethylamino]-ethyl}-4H-benzo[1,4]oxazin-3-one 8-{2-[1,1-dimethyl-2-(2,4,6-trimethylphenyl)-ethylamino]-1-hydroxy-ethyl}-6-hydroxy-4H-benzo[1,4]oxazin-3-one 6-hydroxy-8-{1-hydroxy-2-[2-(4-hydroxy-phenyl)-1,1-dimethyl-ethylamino]-ethyl}-4H-benzo[1,4]oxazin-3-one 6-hydroxy-8-{1-hydroxy-2-[2-(4-isopropyl-phenyl)-1,1dimethyl-ethylamino]-ethyl}-4H-benzo[1,4]oxazin-3-one 8-{2-[2-(4-ethyl-phenyl)-1,1-dimethyl-ethylamino]-1-hydroxy-ethyl}-6-hydroxy-4H-benzo[1,4]oxazin-3-one 8-{2-[2-(4-ethoxy-phenyl)-1,1-dimethyl-ethylamino]-1-hydroxy-ethyl}-6-hydroxy-4H-benzo[1,4]oxazin-3-one 4-(4-{2-[2-hydroxy-2-(6-hydroxy-3-oxo-3,4-dihydro-2H-benzo[1,4]oxazin-8-yl)-ethylamino]-2-methyl-propyl}-phenoxy)-butyric acid 8-{2-[2-(3,4-difluoro-phenyl)-1,1-dimethyl-ethylamino]-1-hydroxy-ethyl}-6-hydroxy-4H-benzo[1,4]oxazin-3-one 1-(4-ethoxy-carbonylamino-3-cyano-5-fluorophenyl)-2-(tert-butylamino)ethanol 2-hydroxy-5-(1-hydroxy-2-{2-[4-(2-hydroxy-2-phenyl-ethylamino)-phenyl]-ethylamino}-ethyl)-benzaldehyde N-[2-hydroxy-5-(1-hydroxy-2-{2-[4-(2-hydroxy-2-phenyl-ethylamino)-phenyl]-ethylamino}-ethyl)-phenyl]-formamide 8-hydroxy-5-(1-hydroxy-2-{2-[4-(6-methoxy-biphenyl-3-ylamino)-phenyl]-ethylamino}-ethyl)-1H-quinolin-2-one 8-hydroxy-5-[1-hydroxy-2-(6-phenethylamino-hexylamino)-ethyl]-1H-quinolin-2-one 5-[2-(2-{4-[4-(2-amino-2-methyl-propoxy)-phenylamino]-phenyl}-ethylamino)-1-hydroxy-ethyl]-8-hydroxy-1H-quinolin-2-one

[3-(4-{6-[2-hydroxy-2-(4-hydroxy-3-hydroxymethyl-phenyl)-ethylamino]-hexyloxy}-butyl)-5-methyl-phenyl]-urea 4-(2-{6-[2-(2,6-dichloro-benzyloxy)-ethoxy]-hexylamino}-1-hydroxy-ethyl)-2-hydroxymethyl-phenol 3-(4-{6-[2-hydroxy-2-(4-hydroxy-3-hydroxymethyl-phenyl)-ethylamino]-hexyloxy}-butyl)-benzylsulphonamide 3-(3-{7-[2-hydroxy-2-(4-hydroxy-3-hydroxymethyl-phenyl)-ethylamino]-heptyloxy}-propyl)-benzylsulphonamide 4-(2-{6-[4-(3-cyclopentanesulphonyl-phenyl)-butoxy]-hexylamino}-1-hydroxy-ethyl)-2-hydroxymethyl-phenol N-Adamantan-2-yl-2-(3-{2-[2-hydroxy-2-(4-hydroxy-3-hydroxymethyl-phenyl)-ethylamino]-propyl}-phenyl)-acetamide optionally in the form of the racemates, enantiomers, diastereomers thereof and optionally in the form of the pharmacologically acceptable acid addition salts, solvates or hydrates thereof. According to the invention the acid addition salts of the betamimetics are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

The anticholinergics used are preferably compounds selected from among the tiotropium salts, preferably the bromide salt, oxitropium salts, preferably the bromide salt, flutropium salts, preferably the bromide salt, ipratropium salts, preferably the bromide salt, glycopyrronium salts, preferably the bromide salt, trospium salts, preferably the chloride salt, tolterodine. In the above-mentioned salts the cations are the pharmacologically active constituents. As anions the above-mentioned salts may preferably contain the chloride, bromide, iodide, sulphate, phosphate, methanesulphonate, nitrate, maleate, acetate, citrate, fumarate, tartrate, oxalate, succinate, benzoate or p-toluenesulphonate, while chloride, bromide, iodide, sulphate, methanesulphonate or p-toluenesulphonate are preferred as counter-ions. Of all the salts the chlorides, bromides, iodides and methanesulphonates are particularly preferred.

Other preferred anticholinergics are selected from among the salts of formula AC-1

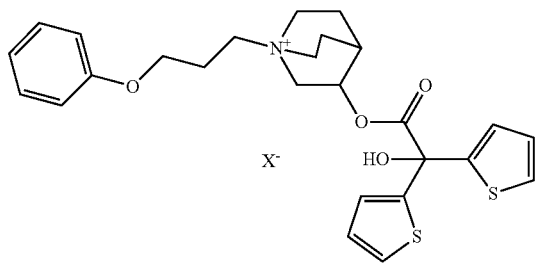

AC-1 wherein $X^-$ denotes an anion with a single negative charge, preferably an anion selected from among the fluoride, chloride, bromide, iodide, sulphate, phosphate, methanesulphonate, nitrate, maleate, acetate, citrate, fumarate, tartrate, oxalate, succinate, benzoate and p-toluenesulphonate, preferably an anion with a single negative charge, particularly preferably an anion selected from among the fluoride, chloride, bromide, methanesulphonate and p-toluenesulphonate, particularly preferably bromide, optionally in the form of the racemates, enantiomers or hydrates thereof. Of particular importance are those pharmaceutical combinations which contain the enantiomers of formula AC-1-en

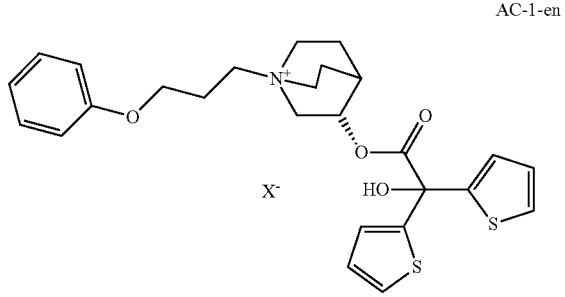

AC-1-en wherein $X^-$ may have the above-mentioned meanings. Other preferred anticholinergics are selected from the salts of formula AC-2

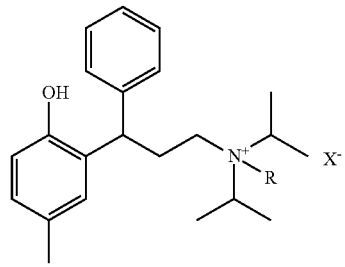

AC-2 wherein R denotes either methyl or ethyl and wherein $X^-$ may have the above-mentioned meanings. In an alternative embodiment the compound of formula AC-2 may also be present in the form of the free base AC-2-base.

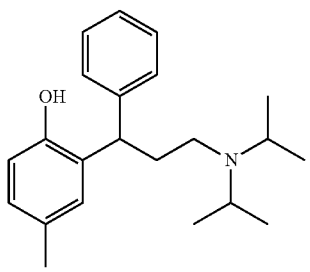

AC-2-base

Other specified compounds are:
  tropenol 2,2-diphenylpropionate methobromide,
  scopine 2,2-diphenylpropionate methobromide,
  scopine 2-fluoro-2,2-diphenylacetate methobromide,
  tropenol 2-fluoro-2,2-diphenylacetate methobromide;
  tropenol 3,3',4,4'-tetrafluorobenzilate methobromide,
  scopine 3,3',4,4'-tetrafluorobenzilate methobromide,
  tropenol 4,4'-difluorobenzilate methobromide,
  scopine 4,4'-difluorobenzilate methobromide,
  tropenol 3,3'-difluorobenzilate methobromide,
  scopine 3,3'-difluorobenzilate methobromide;
  tropenol 9-hydroxy-fluorene-9-carboxylate methobromide;
  tropenol 9-fluoro-fluorene-9-carboxylate methobromide;
  scopine 9-hydroxy-fluorene-9-carboxylate methobromide;
  scopine 9-fluoro-fluorene-9-carboxylate methobromide;
  tropenol 9-methyl-fluorene-9-carboxylate methobromide;
  scopine 9-methyl-fluorene-9-carboxylate methobromide;
  cyclopropyltropine benzilate methobromide;
  cyclopropyltropine 2,2-diphenylpropionate methobromide;
  cyclopropyltropine 9-hydroxy-xanthene-9-carboxylate methobromide;
  cyclopropyltropine 9-methyl-fluorene-9-carboxylate methobromide;
  cyclopropyltropine 9-methyl-xanthene-9-carboxylate methobromide;
  cyclopropyltropine 9-hydroxy-fluorene-9-carboxylate methobromide;
  cyclopropyltropine methyl 4,4'-difluorobenzilate methobromide.
  tropenol 9-hydroxy-xanthene-9-carboxylate methobromide;

scopine 9-hydroxy-xanthene-9-carboxylate methobromide;
tropenol 9-methyl-xanthene-9-carboxylate methobromide;
scopine 9-methyl-xanthene-9-carboxylate methobromide;
tropenol 9-ethyl-xanthene-9-carboxylate methobromide;
tropenol 9-difluoromethyl-xanthene-9-carboxylate methobromide;
scopine 9-hydroxymethyl-xanthene-9-carboxylate methobromide.

The above-mentioned compounds may also be used as salts within the scope of the present invention, wherein instead of the methobromide the metho-X salts are used, wherein X may have the meanings given hereinbefore for $X^-$.

As corticosteroids it is preferable to use compounds selected from among beclomethasone, betamethasone, budesonide, butixocort, ciclesonide, deflazacort, dexamethasone, etiprednol, flunisolide, fluticasone, loteprednol, mometasone, prednisolone, prednisone, rofleponide, triamcinolone, RPR-106541, NS-126, ST-26 and
- (S)-fluoromethyl 6,9-difluoro-17-[(2-furanylcarbonyl)oxy]-11-hydroxy-16-methyl-3-oxo-androsta-1,4-diene-17-carbothionate
- (S)-(2-oxo-tetrahydro-furan-3S-yl)6,9-difluoro-11-hydroxy-16-methyl-3-oxo-17-propionyloxy-androsta-1,4-diene-17-carbothionate,
- cyanomethyl 6α,9α-difluoro-11β-hydroxy-16α-methyl-3-oxo-17α-(2,2,3,3-tertamethylcyclopropylcarbonyl)oxy-androsta-1,4-diene-17β-carboxylate optionally in the form of the racemates, enantiomers or diastereomers thereof and optionally in the form of the salts and derivatives thereof, the solvates and/or hydrates thereof. Any reference to steroids includes a reference to any salts or derivatives, hydrates or solvates thereof which may exist. Examples of possible salts and derivatives of the steroids may be: alkali metal salts, such as for example sodium or potassium salts, sulphobenzoates, phosphates, isonicotinates, acetates, dichloroacetates, propionates, dihydrogen phosphates, palmitates, pivalates or furoates.

PDE4-inhibitors which may be used are preferably compounds selected from among enprofyllin, theophyllin, roflumilast, ariflo (cilomilast), tofimilast, pumafentrin, lirimilast, arofyllin, atizoram, D-4418, Bay-198004, BY343, CP-325.366, D-4396 (Sch-351591), AWD-12-281 (GW-842470), NCS-613, CDP-840, D-4418, PD-168787, T-440, T-2585, V-11294A, C1-1018, CDC-801, CDC-3052, D-22888, YM-58997, Z-15370 and
- N-(3,5-dichloro-1-oxo-pyridin-4-yl)-4-difluoromethoxy-3-cyclopropylmethoxybenzamide
- (−)p-[(4aR*,10bS*)-9-ethoxy-1,2,3,4,4a,10b-hexahydro-8-methoxy-2-methylbenzo[s][1,6]naphthyridin-6-yl]-N,N-diisopropylbenzamide
- (R)-(+)-1-(4-bromobenzyl)-4-[(3-cyclopentyloxy)-4-methoxyphenyl]-2-pyrrolidone
- 3-(cyclopentyloxy-4-methoxyphenyl)-1-(4-N'-[N-2-cyano-S-methyl-isothioureido]benzyl)-2-pyrrolidone
- cis[4-cyano-4-(3-cyclopentyloxy-4-methoxyphenyl)cyclohexane-1-carboxylic acid]
- 2-carbomethoxy-4-cyano-4-(3-cyclopropylmethoxy-4-difluoromethoxy-phenyl)cyclohexan-1-one
- cis[4-cyano-4-(3-cyclopropylmethoxy-4-difluoromethoxyphenyl)cyclohexan-1-ol]
- (R)-(+)-ethyl[4-(3-cyclopentyloxy-4-methoxyphenyl)pyrrolidin-2-ylidene]acetate
- (S)-(−)-ethyl[4-(3-cyclopentyloxy-4-methoxyphenyl)pyrrolidin-2-ylidene]acetate
- 9-cyclopentyl-5,6-dihydro-7-ethyl-3-(2-thienyl)-9H-pyrazolo[3,4-c]-1,2,4-triazolo[4,3-a]pyridine
- 9-cyclopentyl-5,6-dihydro-7-ethyl-3-(tert-butyl)-9H-pyrazolo[3,4-c]-1,2,4-triazolo[4,3-a]pyridine optionally in the form of the racemates, enantiomers or diastereomers thereof and optionally in the form of the pharmacologically acceptable acid addition salts thereof, the solvates and/or hydrates thereof. According to the invention the acid addition salts of the betamimetics are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

The LTD4-antagonists used are preferably compounds selected from among montelukast, pranlukast, zafirlukast, MCC-847 (ZD-3523), MN-001, MEN-91507 (LM-1507), VUF-5078, VUF-K-8707, L-733321 and
- 1-(((R)-(3-(2-(6,7-difluoro-2-quinolinyl)ethenyl)phenyl)-3-(2-(2-hydroxy-2-propyl)phenyl)thio)methylcyclopropane-acetic acid,
- 1-(((1(R)-3(3-(2-(2,3-dichlorothieno[3,2-b]pyridin-5-yl)-(E)-ethenyl)phenyl)-3-(2-(1-hydroxy-1-methylethyl)phenyl)propyl)thio)methyl)cyclopropaneacetic acid
- [2-[[2-(4-tert-butyl-2-thiazolyl)-5-benzofuranyl]oxymethyl]phenyl]acetic acid optionally in the form of the racemates, enantiomers or diastereomers thereof and optionally in the form of the pharmacologically acceptable acid addition salts, solvates and/or hydrates thereof. According to the invention the acid addition salts of the betamimetics are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate. By salts or derivatives which the LTD4-antagonists may optionally be capable of forming are meant, for example: alkali metal salts, such as for example sodium or potassium salts, alkaline earth metal salts, sulphobenzoates, phosphates, isonicotinates, acetates, propionates, dihydrogen phosphates, palmitates, pivalates or furoates.

EGFR-inhibitors which may be used are preferably compounds selected from among cetuximab, trastuzumab, ABX-EGF, Mab ICR-62 and
- 4-[(3-chloro-4-fluorophenyl)amino]-6-{[4-(morpholin-4-yl)-1-oxo-2-buten-1-yl]-amino}-7-cyclopropyl-methoxy-quinazoline
- 4-[(3-chloro-4-fluorophenyl)amino]-6-{[4-(N,N-diethylamino)-1-oxo-2-buten-1-yl]amino}-7-cyclopropyl-methoxy-quinazoline
- 4-[(3-chloro-4-fluorophenyl)amino]-6-{[4-(N,N-dimethylamino)-1-oxo-2-buten-1-yl]amino}-7-cyclopropylmethoxy-quinazoline
- 4-[(R)-(1-phenyl-ethyl)amino]-6-{[4-(morpholin-4-yl)-1-oxo-2-buten-1-yl]-amino}-7-cyclopentyloxy-quinazoline
- 4-[(3-chloro-4-fluoro-phenyl)amino]-6-{[4-((R)-6-methyl-2-oxo-morpholin-4-yl)-1-oxo-2-buten-1-yl]amino}-7-cyclopropylmethoxy-quinazoline
- 4-[(3-chloro-4-fluoro-phenyl)amino]-6-{[4-((R)-6-methyl-2-oxo-morpholin-4-yl)-1-oxo-2-buten-1-yl]amino}-7-[(S)-(tetrahydrofuran-3-yl)oxy]-quinazoline
- 4-[(3-chloro-4-fluoro-phenyl)amino]-6-{[4-((R)-2-methoxymethyl-6-oxo-morpholin-4-yl)-1-oxo-2-buten-1-yl]amino}-7-cyclopropylmethoxy-quinazoline 4-[(3-chloro-4-fluoro-phenyl)amino]-6-[2-((S)-6-methyl-2-oxo-morpholin-4-yl)-ethoxy]-7-methoxy-quinazoline 4-[(3-chloro-4-fluorophenyl)amino]-6-({4-[N-(2-methoxy-ethyl)-N-methyl-amino]-1-oxo-2-buten-1-yl}amino)-7-cyclopropylmethoxy-quinazoline 4-[(3-chloro-4-fluorophenyl)amino]-6-{[4-(N,N-dimethylamino)-1-oxo-2-buten-1-yl]amino}-7-cyclopentyloxy-quinazoline 4-[(R)-(1-phenyl-ethyl)amino]-6-{[4-(N,N-bis-(2-methoxy-ethyl)-amino]-1-oxo-2-buten-1-yl]amino}-7-cyclopropylmethoxy-quinazoline 4-[(R)-(1-phenyl-ethyl)amino]-6-({4-[N-(2-methoxy-ethyl)-N-ethyl-amino]-1-oxo-2-buten-1-yl}amino)-7-cyclopropylmethoxy-quinazoline 4-[(R)-(1-phenyl-ethyl)amino]-6-({4-[N-(2-methoxy-ethyl)-N-methyl-amino]-1-oxo-2-buten-1-yl}amino)-7-cyclopropylmethoxy-quinazoline 4-[(R)-(1-phenyl-ethyl)amino]-6-({4-[N-(tetrahydropyran-4-yl)-N-methyl-amino]-1-oxo-2-buten-1-yl}amino)-7-cyclopropylmethoxy-quinazoline 4-[(3-chloro-4-fluorophenyl)amino]-6-{[4-(N,N-dimethylamino)-1-oxo-2-buten-1-yl]amino}-7-((R)-tetrahydrofuran-3-yloxy)-quinazoline 4-[(3-chloro-4-fluorophenyl)amino]-6-{[4-(N,N-dimethylamino)-1-oxo-2-buten-1-yl]amino}-7-((S)-tetrahydrofuran-3-yloxy)-quinazoline 4-[(3-chloro-4-fluorophenyl)amino]-6-({4-[N-(2-methoxy-ethyl)-N-methyl-amino]-1-oxo-2-buten-1-yl}amino)-7-cyclopentyloxy-quinazoline 4-[(3-chloro-4-fluorophenyl)amino]-6-{[4-(N-cyclopropyl-N-methyl-amino)-1-oxo-2-buten-1-yl]amino}-7-cyclopentyloxy-quinazoline 4-[(3-chloro-4-fluorophenyl)amino]-6-{[4-(N,N-dimethylamino)-1-oxo-2-buten-1-yl]amino}-7-[(R)-(tetrahydrofuran-2-yl)methoxy]-quinazoline 4-[(3-chloro-4-fluorophenyl)amino]-6-{[4-(N,N-dimethylamino)-1-oxo-2-buten-1-yl]amino}-7-[(S)-(tetrahydrofuran-2-yl)methoxy]-quinazoline 4-[(3-ethynyl-phenyl)amino]-6,7-bis-(2-methoxy-ethoxy)-quinazoline 4-[(3-chloro-4-fluorophenyl)amino]-7-[3-(morpholin-4-yl)-propyloxy]-6-[(vinyl-carbonyl)amino]-quinazoline 4-[(R)-(1-phenyl-ethyl)amino]-6-(4-hydroxy-phenyl)-7H-pyrrolo[2,3-d]pyrimidine 3-cyano-4-[(3-chloro-4-fluorophenyl)amino]-6-{[4-(N,N-dimethylamino)-1-oxo-2-buten-1-yl]amino}-7-ethoxy-quinoline 4-{[3-chloro-4-(3-fluoro-benzyloxy)-phenyl]amino}-6-(5-{[(2-methanesulphonyl-ethyl)amino]methyl}-furan-2-yl)quinazoline 4-[(R)-(1-phenyl-ethyl)amino]-6-{[4-((R)-6-methyl-2-oxo-morpholin-4-yl)-1-oxo-2-buten-1-yl]amino}-7-methoxy-quinazoline 4-[(3-chloro-4-fluorophenyl)amino]-6-{[4-(morpholin-4-yl)-1-oxo-2-buten-1-yl]-amino}-7-[(tetrahydrofuran-2-yl)methoxy]-quinazoline 4-[(3-chloro-4-fluorophenyl)amino]-6-({4-[N,N-bis-(2-methoxy-ethyl)-amino]-1-oxo-2-buten-1-yl}amino)-7-[(tetrahydrofuran-2-yl)methoxy]-quinazoline 4-[(3-ethynyl-phenyl)amino]-6-{[4-(5,5-dimethyl-2-oxo-morpholin-4-yl)-1-oxo-2-buten-1-yl]amino}-quinazoline 4-[(3-chloro-4-fluoro-phenyl)amino]-6-[2-(2,2-dimethyl-6-oxo-morpholin-4-yl)-ethoxy]-7-methoxy-quinazoline 4-[(3-chloro-4-fluoro-phenyl)amino]-6-[2-(2,2-dimethyl-6-oxo-morpholin-4-yl)-ethoxy]-7-[(R)-(tetrahydrofuran-2-yl)methoxy]-quinazoline 4-[(3-chloro-4-fluoro-phenyl)amino]-7-[2-(2,2-dimethyl-6-oxo-morpholin-4-yl)-ethoxy]-6-[(S)-(tetrahydrofuran-2-yl)methoxy]-quinazoline 4-[(3-chloro-4-fluoro-phenyl)amino]-6-{2-[4-(2-oxo-morpholin-4-yl)-piperidin-1-yl]-ethoxy}-7-methoxy-quinazoline 4-[(3-chloro-4-fluoro-phenyl)amino]-6-[1-(tert.-butyloxycarbonyl)-piperidin-4-yloxy]-7-methoxy-quinazoline 4-[(3-chloro-4-fluoro-phenyl)amino]-6-(trans-4-amino-cyclohexan-1-yloxy)-7-methoxy-quinazoline 4-[(3-chloro-4-fluoro-phenyl)amino]-6-(trans-4-methanesulphonylamino-cyclohexan-1-yloxy)-7-methoxy-quinazoline 4-[(3-chloro-4-fluoro-phenyl)amino]-6-(tetrahydropyran-3-yloxy)-7-methoxy-quinazoline 4-[(3-chloro-4-fluoro-phenyl)amino]-6-(1-methyl-piperidin-4-yloxy)-7-methoxy-quinazoline 4-[(3-chloro-4-fluoro-phenyl)amino]-6-{1-[(morpholin-4-yl)carbonyl]-piperidin-4-yloxy}-7-methoxy-quinazoline 4-[(3-chloro-4-fluoro-phenyl)amino]-6-{1-[(methoxymethyl)carbonyl]-piperidin-4-yloxy}-7-methoxy-quinazoline 4-[(3-chloro-4-fluoro-phenyl)amino]-6-(piperidin-3-yloxy)-7-methoxy-quinazoline 4-[(3-chloro-4-fluoro-phenyl)amino]-6-[1-(2-acetylamino-ethyl)-piperidin-4-yloxy]-7-methoxy-quinazoline 4-[(3-chloro-4-fluoro-phenyl)amino]-6-(tetrahydropyran-4-yloxy)-7-ethoxy-quinazoline 4-[(3-chloro-4-fluoro-phenyl)amino]-6-((S)-tetrahydrofuran-3-yloxy)-7-hydroxy-quinazoline 4-[(3-chloro-4-fluoro-phenyl)amino]-6-(tetrahydropyran-4-yloxy)-7-(2-methoxy-ethoxy)-quinazoline 4-[(3-chloro-4-fluoro-phenyl)amino]-6-{trans-4-[(dimethylamino)sulphonylamino]-cyclohexan-1-yloxy}-7-methoxy-quinazoline 4-[(3-chloro-4-fluoro-phenyl)amino]-6-{trans-4-[(morpholin-4-yl)carbonylamino]-cyclohexan-1-yloxy}-7-methoxy-quinazoline 4-[(3-chloro-4-fluoro-phenyl)amino]-6-{trans-4-[(morpholin-4-yl)sulphonylamino]-cyclohexan-1-yloxy}-7-methoxy-quinazoline 4-[(3-chloro-4-fluoro-phenyl)amino]-6-(tetrahydropyran-4-yloxy)-7-(2-acetylamino-ethoxy)-quinazoline 4-[(3-chloro-4-fluoro-phenyl)amino]-6-(tetrahydropyran-4-yloxy)-7-(2-methanesulphonylamino-ethoxy)-quinazoline 4-[(3-chloro-4-fluoro-phenyl)amino]-6-{1-[(piperidin-1-yl)carbonyl]-piperidin-4-yloxy}-7-methoxy-quinazoline 4-[(3-chloro-4-fluoro-phenyl)amino]-6-(1-aminocarbonylmethyl-piperidin-4-yloxy)-7-methoxy-quinazoline 4-[(3-chloro-4-fluoro-phenyl)amino]-6-(cis-4-{N-[(tetrahydropyran-4-yl)carbonyl]-N-methyl-amino}-cyclohexan-1-yloxy)-7-methoxy-quinazoline 4-[(3-chloro-4-fluoro-phenyl)amino]-6-(cis-4-{N-[(morpholin-4-yl)carbonyl]-N-methyl-amino}-cyclohexan-1-yloxy)-7-methoxy-quinazoline 4-[(3-chloro-4-fluoro-phenyl)amino]-6-(cis-4-{N-[(morpholin-4-yl)sulphonyl]-N-methyl-amino}-cyclohexan-1-yloxy)-7-methoxy-quinazoline 4-[(3-chloro-4-fluoro-phenyl)amino]-6-(trans-4-ethane-sulphonylamino-cyclohexan-1-yloxy)-7-methoxy-quinazoline
4-[(3-chloro-4-fluoro-phenyl)amino]-6-(1-methane-sulphonyl-piperidin-4-yloxy)-7-ethoxy-quinazoline
4-[(3-chloro-4-fluoro-phenyl)amino]-6-(1-methane-sulphonyl-piperidin-4-yloxy)-7-(2-methoxy-ethoxy)-quinazoline
4-[(3-chloro-4-fluoro-phenyl)amino]-6-[1-(2-methoxy-acetyl)-piperidin-4-yloxy]-7-(2-methoxy-ethoxy)-quinazoline
4-[(3-chloro-4-fluoro-phenyl)amino]-6-(cis-4-acety-lamino-cyclohexan-1-yloxy)-7-methoxy-quinazoline
4-[(3-ethynyl-phenyl)amino]-6-[1-(tert.-butyloxycarbo-nyl)-piperidin-4-yloxy]-7-methoxy-quinazoline
4-[(3-ethynyl-phenyl)amino]-6-(tetrahydropyran-4-yloxy]-7-methoxy-quinazoline
4-[(3-chloro-4-fluoro-phenyl)amino]-6-(cis-4-{N-[(pip-eridin-1-yl)carbonyl]-N-methyl-amino}-cyclohexan-1-yloxy)-7-methoxy-quinazoline
4-[(3-chloro-4-fluoro-phenyl)amino]-6-(cis-4-{N-[(4-methyl-piperazin-1-yl)carbonyl]-N-methyl-amino}-cy-clohexan-1-yloxy)-7-methoxy-quinazoline
4-[(3-chloro-4-fluoro-phenyl)amino]-6-{cis-4-[(morpho-lin-4-yl)carbonylamino]-cyclohexan-1-yloxy}-7-meth-oxy-quinazoline
4-[(3-chloro-4-fluoro-phenyl)amino]-6-{1-[2-(2-oxopyr-rolidin-1-yl)ethyl]-piperidin-4-yloxy}-7-methoxy-quinazoline
4-[(3-chloro-4-fluoro-phenyl)amino]-6-{1-[(morpholin-4-yl)carbonyl]-piperidin-4-yloxy}-7-(2-methoxy-ethoxy)-quinazoline
4-[(3-ethynyl-phenyl)amino]-6-(1-acetyl-piperidin-4-yloxy)-7-methoxy-quinazoline
4-[(3-ethynyl-phenyl)amino]-6-(1-methyl-piperidin-4-yloxy)-7-methoxy-quinazoline
4-[(3-ethynyl-phenyl)amino]-6-(1-methanesulphonyl-pi-peridin-4-yloxy)-7-methoxy-quinazoline
4-[(3-chloro-4-fluoro-phenyl)amino]-6-(1-methyl-piperi-din-4-yloxy)-7(2-methoxy-ethoxy)-quinazoline
4-[(3-chloro-4-fluoro-phenyl)amino]-6-(1-isopropyloxy-carbonyl-piperidin-4-yloxy)-7-methoxy-quinazoline
4-[(3-chloro-4-fluoro-phenyl)amino]-6-(cis-4-methy-lamino-cyclohexan-1-yloxy)-7-methoxy-quinazoline
4-[(3-chloro-4-fluoro-phenyl)amino]-6-{cis-4-[N-(2-methoxy-acetyl)-N-methyl-amino]-cyclohexan-1-yloxy}-7-methoxy-quinazoline
4-[(3-ethynyl-phenyl)amino]-6-(piperidin-4-yloxy)-7-methoxy-quinazoline
4-[(3-ethynyl-phenyl)amino]-6-[1-(2-methoxy-acetyl)-piperidin-4-yloxy]-7-methoxy-quinazoline
4-[(3-ethynyl-phenyl)amino]-6-{1-[(morpholin-4-yl)car-bonyl]-piperidin-4-yloxy}-7-methoxy-quinazoline
4-[(3-chloro-4-fluoro-phenyl)amino]-6-{1-[(cis-2,6-dim-ethyl-morpholin-4-yl)carbonyl]-piperidin-4-yloxy}-7-methoxy-quinazoline
4-[(3-chloro-4-fluoro-phenyl)amino]-6-{1-[(2-methyl-morpholin-4-yl)carbonyl]-piperidin-4-yloxy}-7-meth-oxy-quinazoline
4-[(3-chloro-4-fluoro-phenyl)amino]-6-{1-[(S,S)-(2-oxa-5-aza-bicyclo[2,2,1]hept-5-yl)carbonyl]-piperidin-4-yloxy}-7-methoxy-quinazoline
4-[(3-chloro-4-fluoro-phenyl)amino]-6-{1-[(N-methyl-N-2-methoxyethyl-amino)carbonyl]-piperidin-4-yloxy}-7-methoxy-quinazoline
4-[(3-chloro-4-fluoro-phenyl)amino]-6-(1-ethyl-piperi-din-4-yloxy)-7-methoxy-quinazoline
4-[(3-chloro-4-fluoro-phenyl)amino]-6-{1-[(2-methoxy-ethyl)carbonyl]-piperidin-4-yloxy}-7-methoxy-quinazoline
4-[(3-chloro-4-fluoro-phenyl)amino]-6-{1-[(3-methox-ypropyl-amino)-carbonyl]-piperidin-4-yloxy}-7-meth-oxy-quinazoline
4-[(3-chloro-4-fluoro-phenyl)amino]-6-[cis-4-(N-meth-anesulphonyl-N-methyl-amino)-cyclohexan-1-yloxy]-7-methoxy-quinazoline
4-[(3-chloro-4-fluoro-phenyl)amino]-6-[cis-4-(N-acetyl-N-methyl-amino)-cyclohexan-1-yloxy]-7-methoxy-quinazoline
4-[(3-chloro-4-fluoro-phenyl)amino]-6-(trans-4-methy-lamino-cyclohexan-1-yloxy)-7-methoxy-quinazoline
4-[(3-chloro-4-fluoro-phenyl)amino]-6-[trans-4-(N-methanesulphonyl-N-methyl-amino)-cyclohexan-1-yloxy]-7-methoxy-quinazoline
4-[(3-chloro-4-fluoro-phenyl)amino]-6-(trans-4-dimethy-lamino-cyclohexan-1-yloxy)-7-methoxy-quinazoline
4-[(3-chloro-4-fluoro-phenyl)amino]-6-(trans-4-{N-[(morpholin-4-yl)carbonyl]-N-methyl-amino}-cyclo-hexan-1-yloxy)-7-methoxy-quinazoline
4-[(3-chloro-4-fluoro-phenyl)amino]-6-[2-(2,2-dimethyl-6-oxo-morpholin-4-yl)-methoxy]-7-[(S)-(tetrahydrofu-ran-2-yl)methoxy]-quinazoline
4-[(3-chloro-4-fluoro-phenyl)amino]-6-(1-methane-sulphonyl-piperidin-4-yloxy)-7-methoxy-quinazoline
4-[(3-chloro-4-fluoro-phenyl)amino]-6-(1-cyano-piperi-din-4-yloxy)-7-methoxy-quinazoline optionally in the form of the racemates, enantiomers, diastereomers thereof and optionally in the form of the pharmacologically acceptable acid addition salts, solvates or hydrates thereof. According to the invention the acid addition salts of the betamimetics are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

The dopamine agonists used are preferably compounds selected from among bromocriptine, cabergoline, alpha-dihydroergocryptine, lisuride, pergolide, pramipexole, roxindole, ropinirole, talipexole, terguride and viozan, optionally in the form of the racemates, enantiomers, diastereomers thereof and optionally in the form of the pharmacologically acceptable acid addition salts, solvates or hydrates thereof. According to the invention the acid addition salts of the betamimetics are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydrooxalate, hydrosuccinate, hydrobenzoate and hydro-p-toluenesulphonate.

H1-Antihistamines which may be used are preferably compounds selected from among epinastine, cetirizine, azelastine, fexofenadine, levocabastine, loratadine, mizolastine, ketotifen, emedastine, dimetindene, clemastine, bamipine, cexchlorpheniramine, pheniramine, doxylamine, chlorphenoxamine, dimenhydrinate, diphenhydramine, promethazine, ebastine, desloratidine and meclozine, optionally in the form of the racemates, enantiomers, diastereomers thereof and optionally in the form of the pharmacologically acceptable acid addition salts, solvates or hydrates thereof. According to the invention the acid addition salts of the betamimetics are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

In addition, inhalable macromolecules as disclosed in EP 1 003 478 A1 or CA 2297174 A1 may also be used.

In addition, the compound may be selected from among the ergot alkaloid derivatives, the triptans, the CGRP-inhibitors, the phosphodiesterase-V inhibitors, optionally in the form of the racemates, enantiomers or diastereomers thereof, optionally in the form of the pharmacologically acceptable acid addition salts, the solvates and/or hydrates thereof Examples of ergot alkaloid derivatives are dihydroergotamine and ergotamine.

| List of reference numerals | |
|---|---|
| 1 | nebuliser |
| 2 | fluid |
| 3 | reservoir |
| 4 | fluid chamber |
| 5 | pressure generator |
| 6 | holder |
| 7 | drive spring |
| 8 | locking element |
| 9 | conveying tube |
| 10 | non-return valve |
| 11 | pressure chamber |
| 12 | expulsion nozzle |
| 13 | mouthpiece |
| 14 | aerosol |
| 15 | supply air opening |
| 16 | upper housing part |
| 17 | inner part |
| 17a | upper part of the inner part |
| 17b | lower part of the inner part |
| 18 | housing part (lower part) |
| 19 | holding element |
| 20 | spring (in the lower housing part) |
| 21 | reservoir base |
| 21a | vent opening |
| 22 | piercing element |
| 23 | outer casing |
| 23a | projection |
| 24 | closure |
| 25 | wall |
| 25a | annular region |
| 26 | first closure member |
| 26a | annular groove |
| 26b | contact region |
| 26c | fill opening |
| 27 | second closure member |
| 27a | septum |
| 27b | insertion opening |
| 27c | annular bead |
| 28 | seal |
| 29 | attachment region |
| 30 | barrier |
| 31 | abutment region |
| 32 | angle |
| 33 | axis |
| 34 | transverse seam |
| 35 | longitudinal seam |
| 36 | width |
| 37 | spacing |
| 38 | strip of material |
| 39 | adhesive region |
| 40 | inward fold |
| 41 | part of the transverse seam |
| 42 | part of the transverse seam |

The invention claimed is:

1. A reservoir (3) for a nebuliser (1), the reservoir comprising:
a fluid chamber (4) for a fluid (2) medicament formulation,
a closure (24) that seals the fluid chamber (4), comprising
a first closure member (26) and a second closure member (27), the two closure members (26, 27) being connected to each other in fluidtight manner in an annular attachment region (29) and defining a longitudinal axis (33) of the reservoir, a barrier (30) of annular configuration, spaced radially inwardly, and axially away, from the annular attachment region (29), wherein: (i) the barrier (30) is formed by a snug or press fit of the first and second closure members (26, 27), (ii) the first closure member (26) includes an annular conical section initiating at a first annular edge and extending conically, radially, and inwardly to a second annular edge, and (iii) the second closure member (27) includes an annular engagement portion configured to engage the annular conical section of the first closure member (26) between the first and second annular edge thereof, such that the first and second closure members (26,27) conically engage one another in an abutment region (31), wherein the abutment region (31) is defined by the annular conical section of the first closure member (26) being inclined relative to the longitudinal axis of the reservoir (3), and the barrier (30) arranged on a fluid side with respect to the attachment region (29) to prevent the ingress of any particles produced during the attachment of the closure members (26, 27) or other contaminants into the fluid (2) and/or into the fluid chamber (4).

2. The reservoir according to claim 1, wherein the first and second closure members (26, 27) are welded to each other in the attachment region (29) by at least one of: (i) material of the first and/or second closure member (26, 27), (ii) an additional material, (iii) an additional material in the form of a powder, and (iv) an additional material in the form of a ring.

3. The reservoir according to claim 1, wherein the attachment region (29) and the barrier (30) are concentric about the longitudinal axis.

4. The reservoir according to claim 1, wherein the attachment region (29) seals the fluid chamber (4) in a gastight manner after the fluid (2) has been introduced.

5. The reservoir according to claim 1, wherein the barrier (30) is spaced away from the attachment region (29) axially along the longitudinal axis in a direction toward an interior of the reservoir (3).

6. The reservoir according to claim 1, wherein the annular engagement portion of the second closure member (27) includes an annular discontinuity which engages the annular conical section of the first closure member (26) between the first and second annular edge thereof in the area of conical engagement.

7. The reservoir according to claim 1, wherein the annular conical section of the first closure member (26) is inclined at an angle of about 15° to the longitudinal axis.

8. The reservoir according to claim 1, wherein the annular conical section of the first closure member (26) is inclined relative to the longitudinal axis of the reservoir (3), toward a direction of assembly of the first and second closure members (26, 27), and toward an axis perpendicular to a flat extent of the attachment region (29), and/or toward a direction of insertion of a conveying element into the reservoir (3).

9. The reservoir according to claim 1, wherein the barrier (30) is formed only by the first and second closure members (26, 27).

10. The reservoir according to claim 1, wherein the fluid chamber (4) has a flexible or deformable wall (25), so that when fluid (2) is taken out the fluid chamber (4) collapses and/or forms a deformable inner container.

11. The reservoir according to claim 10, wherein the first closure member (26) is attached to the wall (25) and the wall (25) is firmly attached only to the first closure member (26).

12. The reservoir according to claim 10, wherein at least one of: (i) the fluid chamber (4) or the wall (25) thereof has a greater width (36) at a free end remote from the closure (24) as compared with an end towards the closure (24), (ii) the wall (25) has a longitudinal seam (35), wherein longitudinal edges of a piece of material that forms the wall (25) are joined together at least substantially edge to edge by means of an additional strip of material (38).

13. The reservoir according to claim 10, wherein the fluid chamber (4) is at least partly or substantially in the form of a bag or flexible tube.

14. The reservoir according to claim 1, wherein the closure (24) can be opened by attaching or inserting a conveying tube (9), for removing fluid (2) from the reservoir (3).

15. A nebuliser (1) for inhalation of a medical aerosol in the form of a fluid (2) having a reservoir (3) with the fluid (2) according to claim 1.

16. The reservoir of claim 1, wherein attachment of the first and second closure members (26, 27) in the attachment region (29) is achieved through axial movement of the second closure member (27) relative to the first closure member (26) and such axial movement puts the barrier (30) into operation.

* * * * *